United States Patent [19]

Lednicer et al.

[11] Patent Number: 4,888,353
[45] Date of Patent: Dec. 19, 1989

[54] CARBOXAMIDES USEFUL AS ANTIEMETIC OR ANTIPSYCHOTIC AGENTS

[75] Inventors: Daniel Lednicer, Columbia, Mo.; Jung-Hui Sun, Dublin, Ohio

[73] Assignee: Erbamont, Inc., Minn.

[21] Appl. No.: 868,899

[22] Filed: May 23, 1986

Related U.S. Application Data

[63] Continuation of Ser. No. 835,006, Feb. 28, 1986, abandoned, which is a continuation-in-part of Ser. No. 564,641, Dec. 22, 1983, abandoned.

[51] Int. Cl.$^4$ ............... A61K 31/40; C07D 498/02
[52] U.S. Cl. .................... 514/422; 514/466; 514/304; 548/525; 548/400; 549/462; 549/471; 546/126; 564/161; 564/180; 564/189
[58] Field of Search .............. 548/525, 400; 549/462, 549/471; 546/126; 514/422, 466, 304; 564/161, 180, 189

[56] References Cited

U.S. PATENT DOCUMENTS

| | | | |
|---|---|---|---|
| 3,342,826 | 9/1967 | Miller et al. | 260/294 |
| 3,745,175 | 7/1973 | Thominet | 260/326.3 |
| 3,860,619 | 1/1975 | Christensen et al. | 260/346.2 R |
| 4,205,080 | 5/1980 | Carr | 424/275 |
| 4,207,327 | 1/1980 | Lunsford et al. | 424/273 |
| 4,617,314 | 10/1986 | Tahara et al. | 548/518 |
| 4,717,563 | 1/1988 | Alphih et al. | 424/10 |
| 4,722,834 | 2/1988 | Teng et al. | 424/10 |
| 4,772,459 | 9/1988 | Suh et al. | 424/10 |

FOREIGN PATENT DOCUMENTS

| | | |
|---|---|---|
| 0068700 | 1/1983 | European Pat. Off. . |
| 0095262 | 11/1983 | European Pat. Off. . |
| 0099789 | 2/1984 | European Pat. Off. . |
| 0124783 | 11/1984 | European Pat. Off. . |
| 0158532 | 10/1985 | European Pat. Off. . |
| 2325370 | 4/1977 | France . |
| 2396757 | 2/1979 | France . |
| WO84/00166 | 1/1984 | PCT Int'l Appl. . |
| WO84/03281 | 8/1984 | World Int. Prop. O. . |

*Primary Examiner*—Mukund J. Shah
*Assistant Examiner*—C. L. Cseh
*Attorney, Agent, or Firm*—Smith & Schnacke

[57] ABSTRACT

Carboxamides represented by the formula (I):

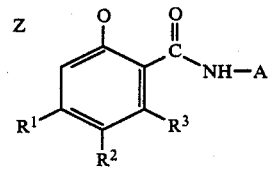

wherein Z represents the carbon atoms necessary to complete a 5- to 7-membered ring, $R^1$, $R^2$, and $R^3$ may be the same or different and are selected from the group consisting of a hydrogen atom, a lower alkyl group, a cycloalkyl group, a halogen atom, an amino group, a lower alkylamino group, an alkoxy group, an acylamido group, a sulfonamido group, and a nitro group; and A represents an aminoalkyl moiety and acid addition salts thereof.

37 Claims, No Drawings

CARBOXAMIDES USEFUL AS ANTIEMETIC OR ANTIPSYCHOTIC AGENTS

CROSS-REFERENCE TO RELATED APPLICATION

This is a continuation-in-part of U.S. application Ser. No. 835,006 filed Feb. 28, 1986, which in turn is a continuation-in-part of U.S. application Ser. No. 564,641 filed Dec. 22, 1983 both now abandoned.

BACKGROUND OF THE INVENTION

The present invention relates to a novel group of benzamides which are useful as antiemetic and/or antipsychotic agents. More particularly, it relates to a novel group of benzofuran-7-carboxamides.

There has been little treatment in the literature of the relationship between structure and activity of antiemetic and antipsychotic agents. A large number of chemically quite diverse compounds have been used particularly as antiemetic agents. This is due to the fact that there is more than one physiological cause for these disorders.

U.S. Pat. No. 3,342,826 discloses a number of benzamide derivatives which are useful antipsychotic and antiemetic agents. Among the compounds disclosed in the patent is sulpiride, 2-methoxy-N-(1-ethyl-2-pyrrolidinylmethyl)-5-sulfamoyl benzamide. U.S. Pat. No. 3,177,252 to Thominet discloses metoclopramide, 4-amino-5-chloro-N-[(2-diethylamino)ethyl]-2-methoxybenzamide, which has been used clinically to prevent emesis.

Benzamide derivatives function as antiemetic and antipsychotic agents by blocking dopamine receptors in the brain. The administration of sulpiride, metoclopramide, and other prior benzamide derivatives is accompanied by several undesirable side effects including an increase in the release of prolactin and extrapyramidal side effects. It is believed that in blocking certain dopamine receptors benzamide derivatives prevent the secretion of prolactin inhibiting factor or PIF, which regulates the release of prolactin. As a result, there is an elevation in prolactin levels and mammary hypertrophy in the form of breast engorgement, galactorrhea, and amenorrhea results.

Thus, there is a need for effective antiemetic and antipsychotic agents and, particularly, for antiemetic and antipsychotic agents which are free from the aforementioned side effects.

SUMMARY OF THE INVENTION

The principal object of the present invention is to provide carboxamides which are useful as antiemetic and/or antipsychotic agents and pharmaceutical preparations containing the same.

In the case of benzamide derivatives, it appears that the 2-methoxy group located adjacent to the carboxamide linkage in both sulpiride and metoclopramide plays an important role in providing good antipsychotic and antiemetic activity. The compounds of the present invention are characterized in that an oxygen atom in a saturated or unsaturated ring is adjacent the carboxamide linkage.

The compounds of the present invention are represented by the general formula (I):

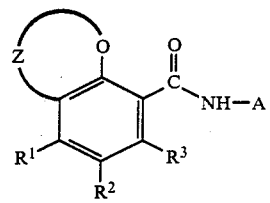

wherein Z represents the carbon and hydrogen atoms necessary to complete a substituted or unsubstituted, saturated or unsaturated, 5- to 7-membered ring and, more particularly, a benzo[b]furan or a dihydrobenzo[b]furan ring; $R^1$, $R^2$, and $R^3$ may be the same or different and represent a member selected from the group consisting of a hydrogen atom, a lower alkyl group, a cycloalkyl group, a lower alkoxy group, an amino group, a lower alkyl substituted amino group, an acylamido group (e.g., having 1 to 6 carbon atoms), a sulfonamido group (e.g., having up to 6 carbon atoms), a halogen atom, and a nitro group; A represents an aminoalkyl group.

Typical examples of the groups represented by A in formula (I) are:

(IV)

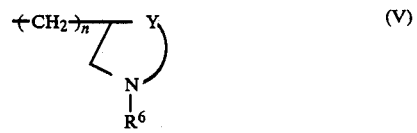

(V)

(VI)

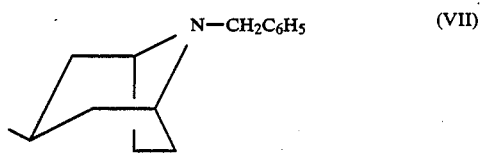

(VII)

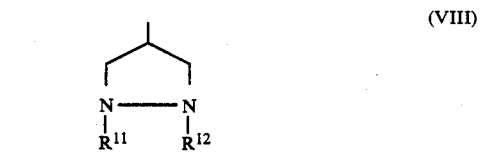

(VIII)

(X)

wherein W represents a single bond or the carbon and hydrogen atoms necessary to complete a 3- to 8-membered saturated or unsaturated ring and preferably a 5-membered ring; Y represents a single bond or the carbon and hydrogen atoms necessary to complete a 4 to 8 membered saturated or unsaturated ring; $R^6$ is selected from the group consisting of a hydrogen atom, a lower alkyl group, a phenyl group, a phenalkyl group, a fluorine-substituted alkyl group such as a trifluoromethyl group or a 2,2,2-trifluoroethyl group, a propargyl group, and an allyl group; $R^7$ and $R^8$ may be the same or different and selected from the group consisting of a hydrogen atom, a lower alkyl group, and a lower hydroxyalkyl group; $M^1$ and $M^2$ are the same or different and represent a hydrogen atom or a methyl group; $R^{11}$ and $R^{12}$ are the same or different and represent a lower alkyl group, a cycloalkyl group, or a phenalkyl group, and n is 0 or an integer of 1 to 3.

More particularly, A may be represented by the formula:

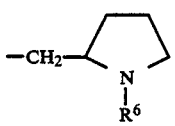
(IVa)

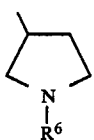
(Va)

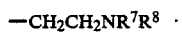
—CH$_2$CH$_2$NR$^7$R$^8$    (VIa)

where $R^6$, $R^7$ and $R^8$ are defined as above.

The present invention is more specifically directed to benzo[b]furan and dihydrobenzo[b]furancarboxamides represented by the formulas (II) and (III) wherein $R^1$, $R^2$, and $R^3$ are defined as above and $R^9$, $R^{9A}$, and $R^{9B}$ are selected from the group consisting of a hydrogen atom, an alkyl group having 1 to 3 carbon atoms, or a phenyl group, and to pharmaceutical preparations containing the same. $R^9$, $R^{9A}$, and $R^{9B}$ may be at the 2- or 3-position.

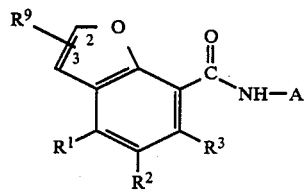
(II)

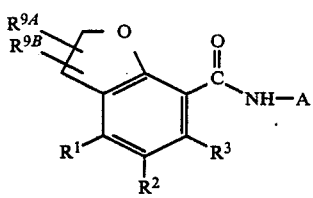
(III)

The present invention is still more specifically directed to compounds of the formulae (I), (II), or (III) wherein A is represented by the formula (IVa) and to pharmaceutical compositions containing the same. Compounds are particularly preferred in which A is represented by the formula (IVa) and $R^2$ is a chlorine atom, an amino group or a lower alkyl group, and $R^1$ and $R^3$ are hydrogen, or $R^1$ is amino, $R^2$ is chloro, and $R^3$ is hydrogen.

The non-toxic pharmaceutically-acceptable acid addition salts of the compound are also included within the scope of this invention, as well as the racemates and separated optical isomers.

DETAILED DESCRIPTION OF THE INVENTION

With reference to formula (I) above, in more detail Z represents the atoms necessary to complete a 5- to 7-membered saturated or unsaturated oxygen containing ring. While 6- and 7-membered rings are functional, in the preferred compounds Z forms a benzo[b]furan or a dihydrobenzo[b]furan ring which may be substituted in the 2- or 3-position by a lower alkyl group such as a methyl group or an ethyl group or by a phenyl group, or which may be unsubstituted. Where Z represents the atoms necessary to form a dihydrobenzo[b]furan ring, Z may be represented by the formula $C_nH_{2n}$ where n is 2 to 4 such as —CH$_2$CH$_2$—, —CH$_2$CH(CH$_3$)—, —CH$_2$C(CH$_3$)$_2$—, —CH(CH$_3$)CH$_2$—, —CH$_2$CH(C$_2$H$_5$)—, etc. Where Z represents the atoms necessary to form a benzofuran ring, Z may represent —CH═CH—, —CH═CCH$_3$—, or —CH$_3$C═CH—. Alternatively, Z may include a phenyl group at the 2- or 3-position.

The term "lower alkyl group" as used herein includes straight or branched chain alkyl groups of about 1 to 6 carbon atoms such as methyl, ethyl, propyl, i-propyl, n-butyl, t-butyl, amyl, isoamyl, n-hexyl, etc.

The term "lower alkoxy group" as used herein includes alkoxy groups which correspond to the aforementioned alkyl groups with the addition of the —O— linkage.

The term "phenyl group" and "phenalkyl group" include groups in which the phenyl moiety is unsubstituted or substituted by substituents such as methyl, ethyl, propyl, butyl, fluoro, chloro, bromo, iodo, amino, hydroxyl, methoxy, ethoxy, cyano, acetamido, sulfamoxyl, and trifluoromethyl. Examples of phenalkyl groups include benzyl, phenethyl and phenypropyl groups.

The term "cycloalkyl group" includes cycloalkyl groups containing up to 12 carbon atoms and preferably 4 to 8 carbon atoms such as cyclobutyl, cyclohexyl, cyclopentyl, and ethylcyclohexyl.

Representative examples of the alkyl group represented by $R^1$, $R^2$, or $R^3$ include methyl, ethyl, n-propyl, i-propyl, and t-butyl groups.

Representative examples of the halogen atoms represented by $R^1$, $R^2$, and $R^3$ include fluorine, chlorine, bromine and iodine atoms.

The amino group represented by $R^1$, $R^2$, or $R^3$ may be an unsubstituted amino group or a substituted amino group of the formula -NR$^4$R$^5$ wherein $R^4$ and $R^5$ may be the same or different and selected from a hydrogen atom or a lower alkyl group. Otherwise, the amino group can be a substituted amino group such as an acylamido (e.g., acetamido) or a sulfonamido group of the formulae -NHCOR$^4$ and -NHSO$_2$R$^4$ wherein $R^4$ is defined as above.

Representative examples of the alkoxy groups for $R^1$, $R^2$, and $R^3$ include methoxy, ethoxy, and propoxy.

In the general formulae (I-III), A represents an aminoalkyl group. In several of the compounds of the present invention, A represents an aminoalkyl group having the atomic sequence:

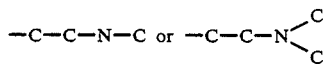

and preferably a group of the formulae (IV-VIII and X) above.

In the formula (IV), W most preferably represents the atoms necessary to complete a pyrrolidinyl ring. A particularly advantageous compound is obtained when $R^6$ in formula (IVa) represents a hydrogen atom such that A is a 2-pyrrolidinylmethyl group. This compound does not exhibit antipsychotic activity and can therefore be administered as an antiemetic agent without antipsychotic effects. Otherwise, $R^6$ is preferably ethyl, benzyl, allyl, or propargyl.

In formula (V), Y may represent the atoms necessary to complete a pyrrolidinyl ring, and $R^6$ may be benzyl.

In formula (VI), $M^1$ and $M^2$ are preferably hydrogen and $R^7$ and $R^8$ are both ethyl, both hydroxyethyl, or one of $R^7$ and $R^8$ is ethyl and the other hydroxyethyl.

In formula (VIII), $R^{11}$ and $R^{12}$ may be the same or different and represent a methyl group, an ethyl group, an isopropyl group, a cyclobutyl group, a cyclopentyl group, a cyclohexyl group, and ethylcyclohexyl group, a benzyl group, a lower alkyl sutstituted benzyl group, a phenethyl group, or a phenpropyl group.

Particularly preferred compounds are compounds in which A has the formula (IV), W forms a pyrrolidinyl ring as shown in formula (IVa) and $R^1$, $R^2$, and $R^3$ are defined as in the following table.

| | | |
|---|---|---|
| $R^1 = H$ | $R^2 = Cl$ | $R^3 = H$ |
| $R^1 = H$ | $R^2 = NH_2$ | $R^3 = H$ |
| $R^1 = NH_2$ | $R^2 = Cl$ | $R^3 = H$ |
| $R^1 = H$ | $R^2 = H$ | $R^3 = OCH_3$ |

The compounds of the present invention exhibit antipsychotic and antiemetic activity in in vivo screening tests as shown below. The compounds can be compounded with a suitable pharmaceutical carrier for parenteral or oral administration. In most cases the compounds are useful in the form of the acid addition salt, e.g., the hydrochloride, phosphate, fumarate, citrate, tartarate. Therapeutically-effective dosages will lie in the range of about 0.01 to 10 mg/kg.

Many of the compounds of the present invention contain an asymmetric carbon atom and have optical d and l isomers. These compounds can be used as the dl racemate or the d- or l-isomer can be separately synthesized from optically pure starting material or separated from the racemate in a conventional manner. In preliminary studies a tendency for the l-isomer to be more active than the racemate has been noted.

Representative examples of compounds in accordance with the present invention are provided in the following Table.

TABLE

1.
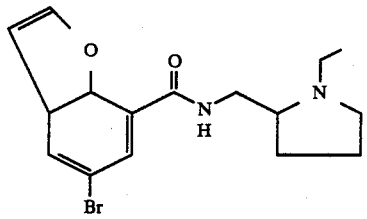

2.
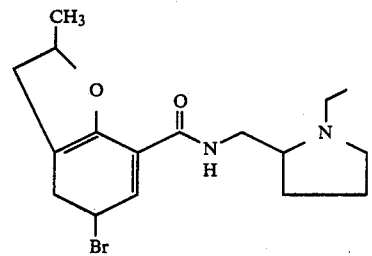

3.
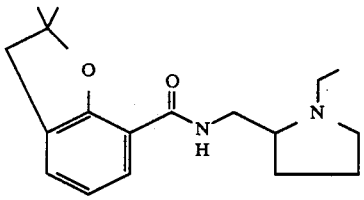

4.
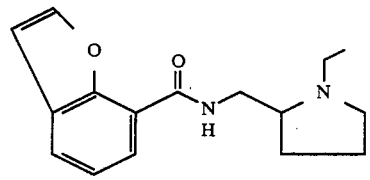

5.
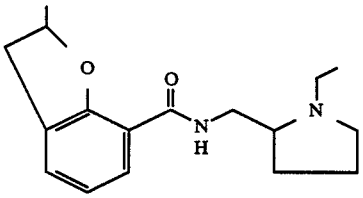

6.
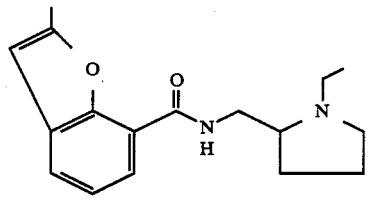

7.
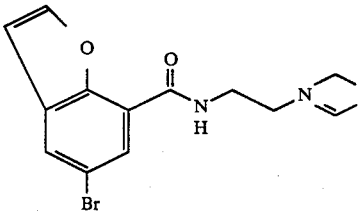

8.
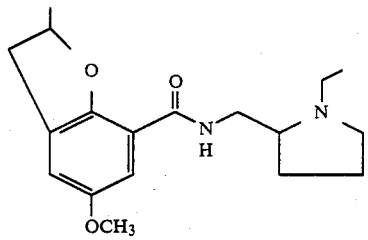

TABLE-continued
9. 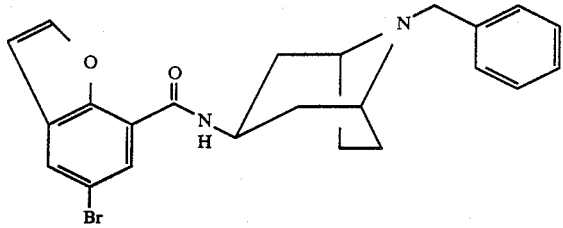
10. 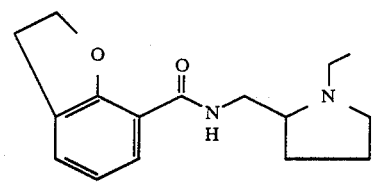
11. 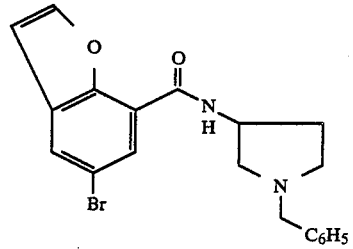
12. 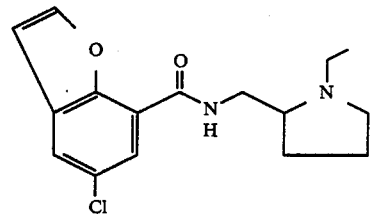
13. 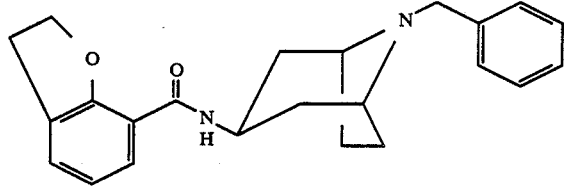
14. 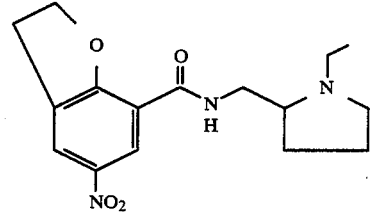
15. 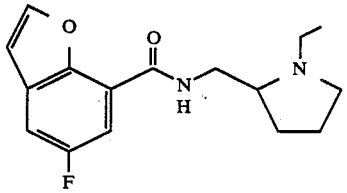
16. 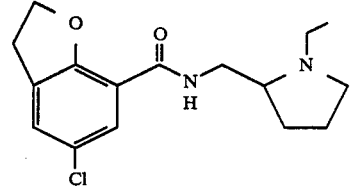
17. 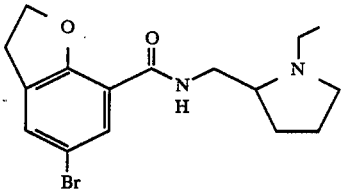
18. 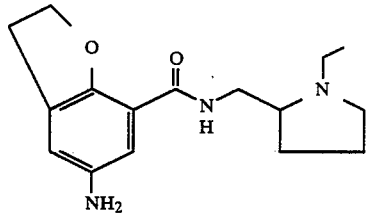
19. 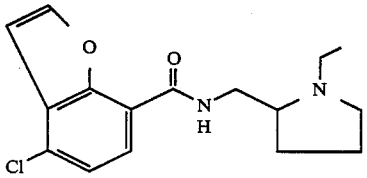
20. 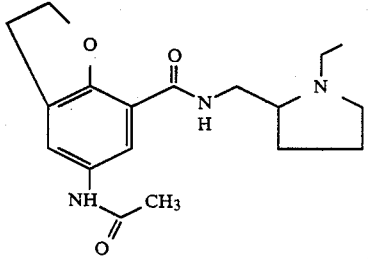

TABLE-continued
21. 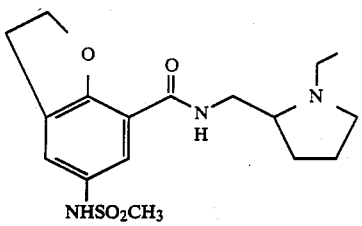
22. 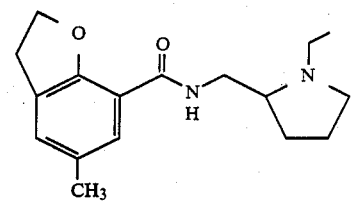
23. 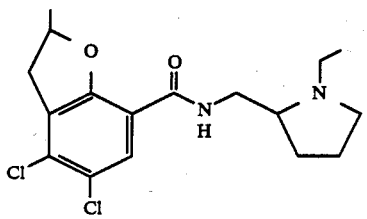
24. 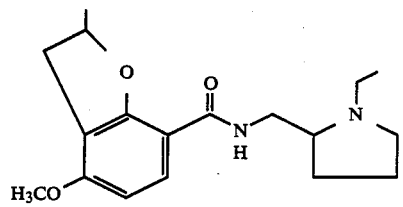
25. 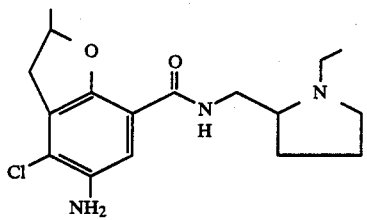
26. 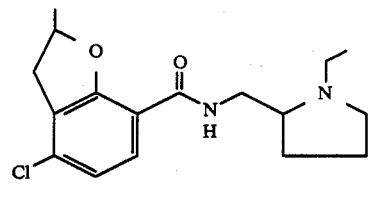
27. 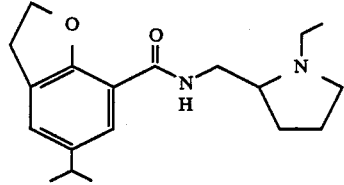
28. 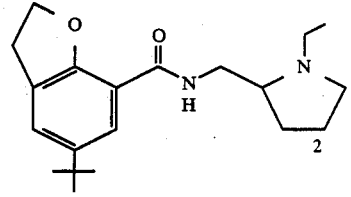
29. 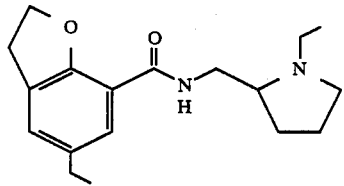
30. 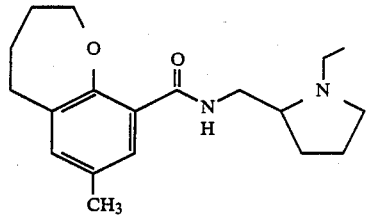
31. 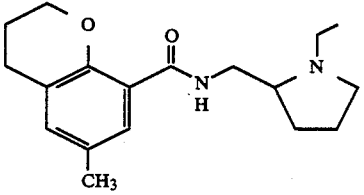
32. 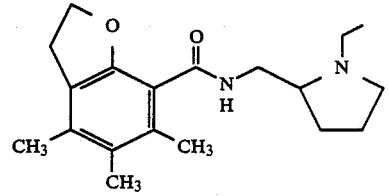
33. 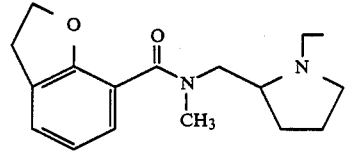
34. 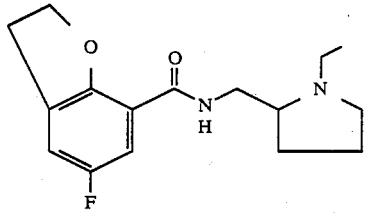

TABLE-continued
| | | | |
|---|---|---|---|
| 35. | 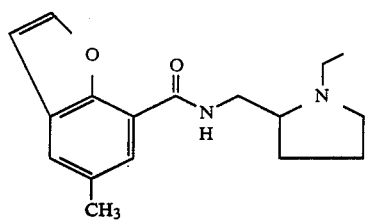 | 36. | 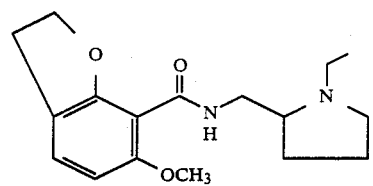 |
| 37. | 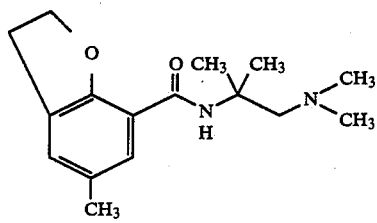 | 38. | 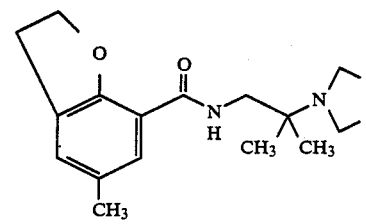 |
| 39. | 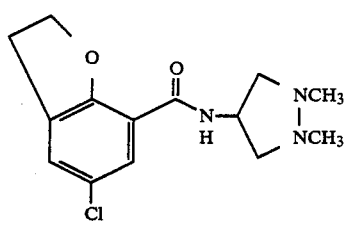 | 40. | 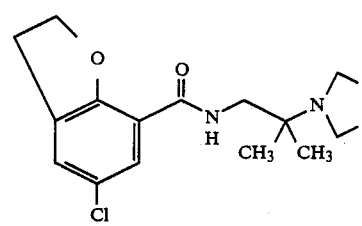 |
| 41. | 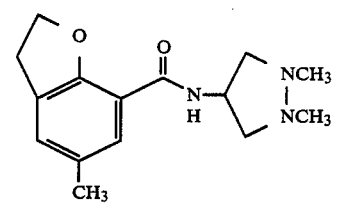 | 42. | 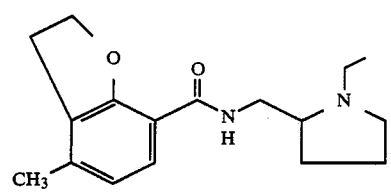 |
| 43. | 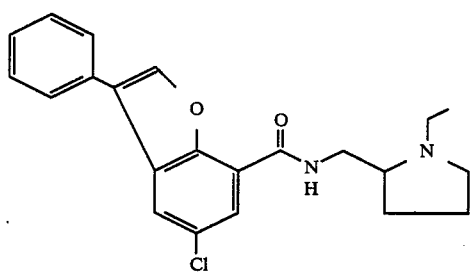 | 44. | 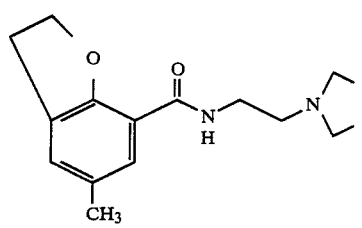 |
| 45. | 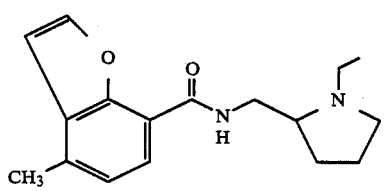 | 46. | 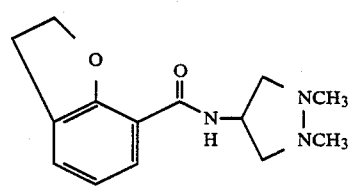 |
| 47. | 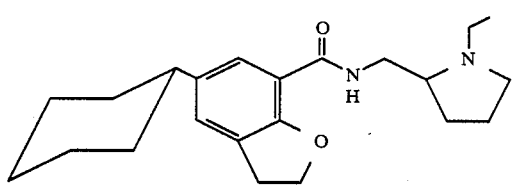 | 48. | 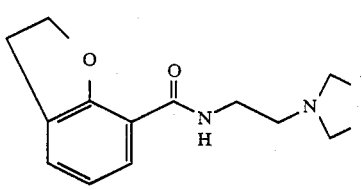 |

TABLE-continued
| | | | |
|---|---|---|---|
| 49. | 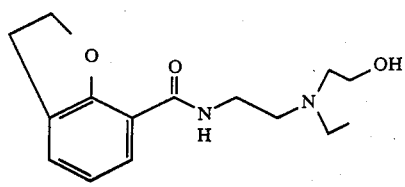 | 50. | 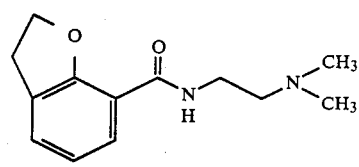 |
| 51. | 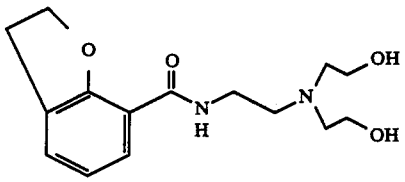 | 52. | 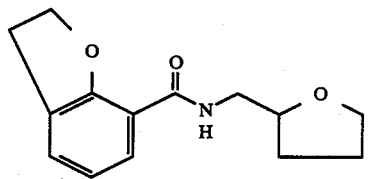 |
| 53. | 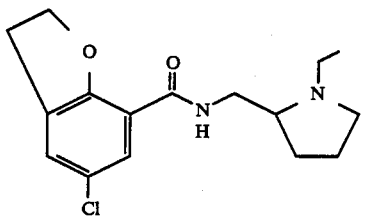 | 54. | 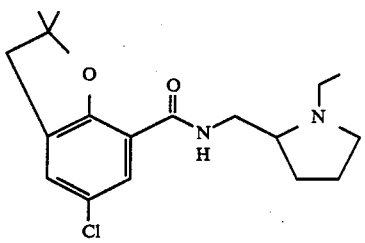 |
| 55. | 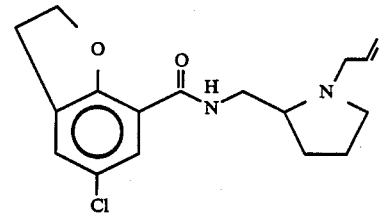 | 56. | 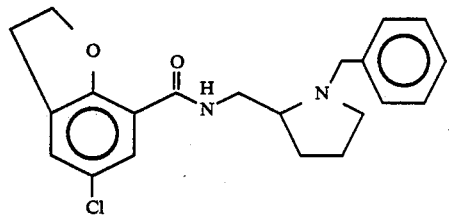 |
| 57. | 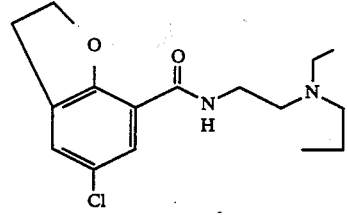 | 58. | 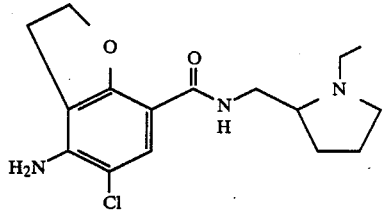 |
| 59. | 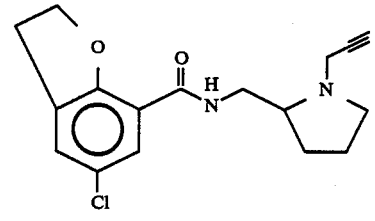 | 60. | 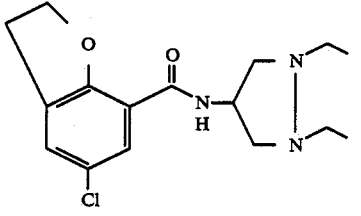 |
| 61. | 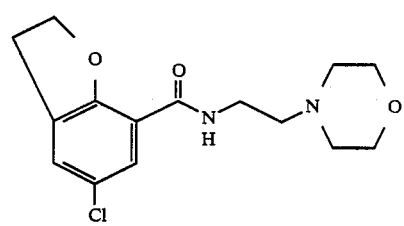 | 62. | 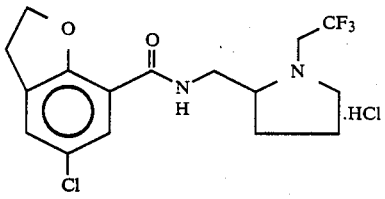 |

TABLE-continued
63. 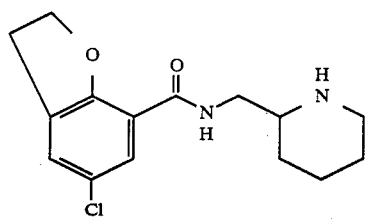
64. 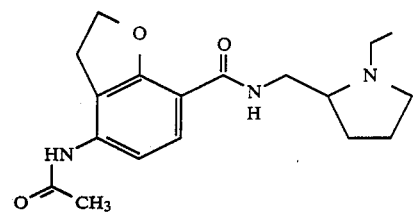
65. 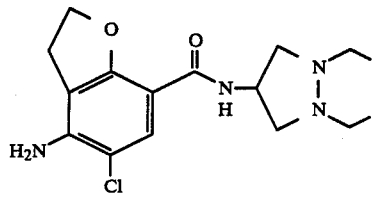
66. 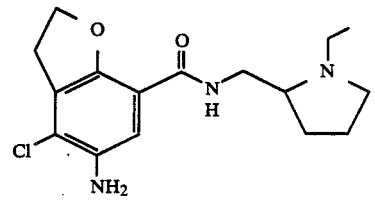
67. 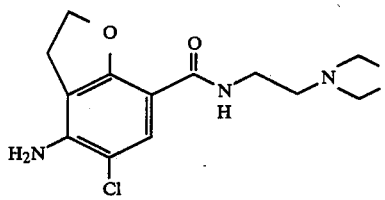
68. 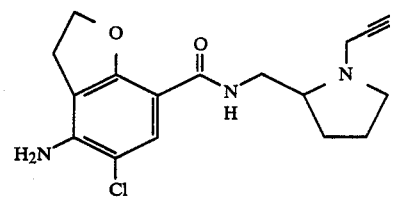
69. 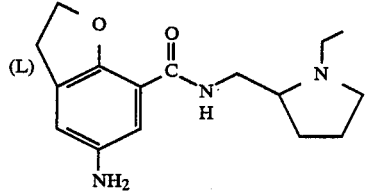
70. 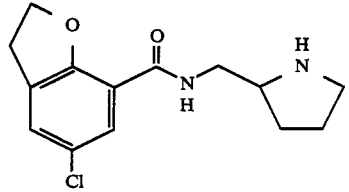
(racemate)
71. 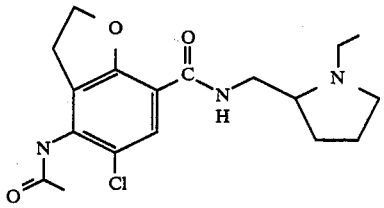
72. 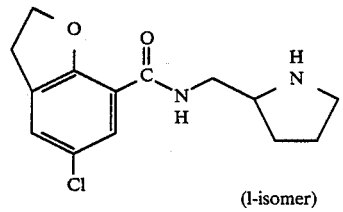
(l-isomer)
73. 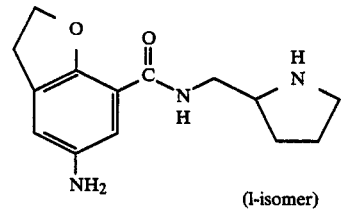
(l-isomer)
74. 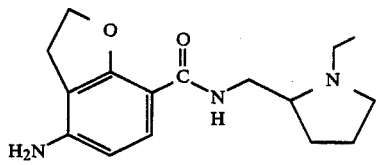
75. 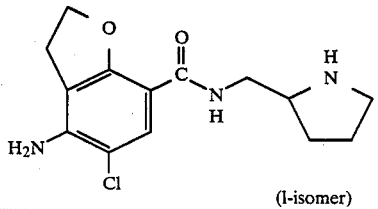
(l-isomer)

TABLE I

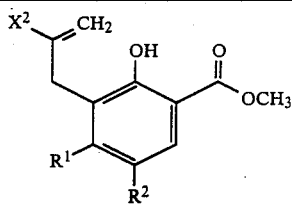

| Compounds | $R^1$ | $R^2$ | $X^2$ | Method | Claisen Rearrangement temp (°C.) | Reaction time (hr) | Yield (%) | bp (mm) | Formula (Calc'd) |
|---|---|---|---|---|---|---|---|---|---|
| 4a | H | H | H | A | 195–200 | 16 | 92.5 | 80–95(0.02) | $C_{11}H_{12}O$ |
| 4b | H | Br | H | A | 190 | 20 | 89.4 | 110–126(0.25–0.5) | $C_{11}H_{11}BrO_3$ |
| 4c | H | Cl | H | A | 200 | 20 | 88.5 | 130–136(3.5) | $C_{11}H_{11}ClO_3$ |
| 4d | H | F | H | A | 190–200 | 20 | 88.0 | 83–89(1.0) | $C_{11}H_{11}FO_3$ |
| 4e | H | $OCH_3$ | H | A | 205 | 64 | 87.0 | 142–144(3.0) | $C_{12}H_{14}O_4$ |
| 4f | Cl | H | H | A | 200 | 38 | 32.9 | 117–121 | $C_{11}H_{11}ClO_3$ |
|  |  |  |  | B | 190–205 | 20 | 71.1 |  |  |
| 4g | $OCH_3$ | H | H | B | 190–205 | 18 | 59.5 | 55–58 (mp) | $C_{12}H_{14}O_4$ |
| 4h | H | H | $CH_3$ | A | 200 | 18 | 90.8 | 102–108(3.0) | $C_{12}H_{14}O_3$ |

In many instances, the compounds of the present invention can be prepared by condensing benzo[b]furan-7-carboxylic acid or dihydrobenzo[b]furan-7-carboxylic acid chlorides or esters with appropriate amines and recovering the carboxamides as acid salts. An alternative method of preparing the compounds utilizes an appropriately substituted benzofuran carboxylic acid which is reacted with ethyl chloroformate to form a mixed anhydride of the acid which is subsequently reacted with a solution of the amine (e.g., in dichloromethane). This method simplifies the synthesis where the carboxylic acid includes one or more substituents, such as an amino group, which is capable of reacting with the carboxyl group in competition with the amine. Hereinbelow, four synthetic approaches to the carboxamides are described.

The synthesis of the benzofuran-7-carboxylic acid esters, which are convertible to the acid chloride to produce benzofurancarboxamides in accordance with the present invention proceeds along Reaction Scheme I:

Reaction Scheme I

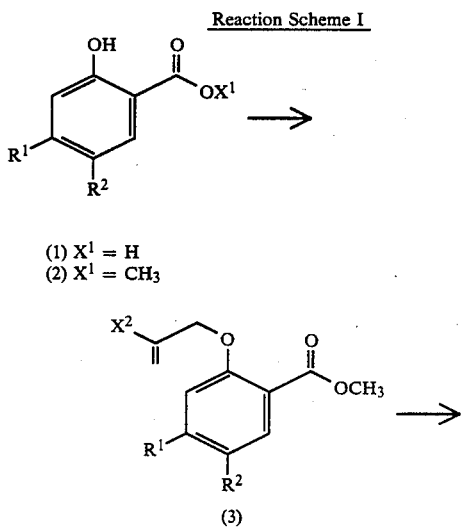

(1) $X^1$ = H
(2) $X^1$ = $CH_3$ (3)

-continued
Reaction Scheme I

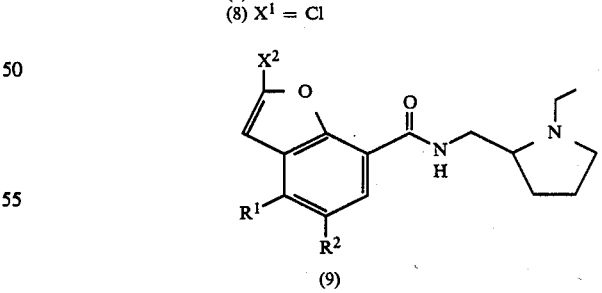

(4) Y = $CH_2$
(5) Y = O

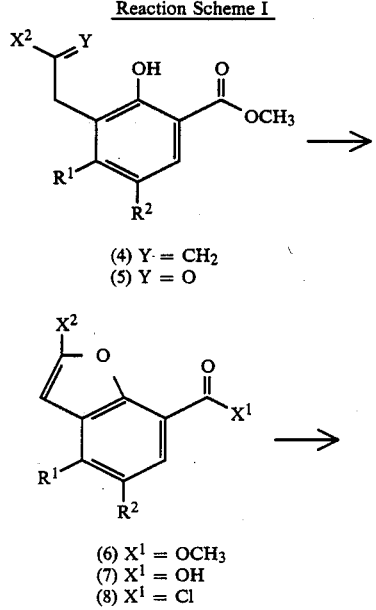

(6) $X^1$ = $OCH_3$
(7) $X^1$ = OH
(8) $X^1$ = Cl

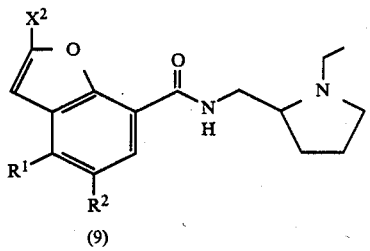

(9)

The compounds of the present invention can be prepared from commercially available substituted or unsubstituted salicylic acids. In accordance with Reaction Scheme I, 2-, 3-, 4-, 5-, or 6-substituted or unsubstituted benzofuran-7-carboxamides can be synthesized from salicylic acid (1) by treating the acid with methanol in the presence of sulfuric acid as a catalyst, to produce the methyl ester (2), the ester (2) can be alkylated to give the intermediate (3) in over 90% yield by nucleophilic substitution of the phenoxide ion with an allyl halide in acetone containing potassium carbonate. The 2-unsubstituted derivatives are prepared by substitution with allyl bromide. The 2- or 3-alkyl substituted derivatives are prepared by reacting with 3-chloro-2-alkyl propene or 3-chloro-3-alkyl propene. The products are clean and can be used for subsequent reaction without purification.

By heating the intermediate (3) at about 200° C. under argon either without any solvent (Method A) or with N,N-dimethylaniline (Method B), a Claisen rearrangement takes place resulting in the compound (4). Table I below summarizes the Claisen rearrangement conditions for obtaining eight intermediates (Compounds 4a-4h) by this method and provides the relevant analytical data. Attempts to distill compounds (4f) and (4g) led to mixtures possibly due to production of para isomers by further rearrangement. Chromatography of the reaction mixture (4g) gave the desired compound (4g) along with the p-isomer in 3.7% yield. Column chromatography of compound (4f) led to isolation of four products including compound (4f).

The intermediate (4) can be oxidized by reaction with $OsO_4/NaIO_4$ in ethyl ether and water at room temperature to produce the corresponding aldehydes or ketones (5) in very good yields. Due to the instability of the aldehydes and ketones (5), they are carried to the next step (acid-catalyzed cyclization) without purification.

Acid catalysts are employed for cyclization of the aldehydes or ketones to produce compound (6). The acid catalysts of choice are either Amberlyst-XN1010 and trifluoroacetic acid (TFA). TFA is more preferred because it requires a shorter reaction time and generates fewer by-products. Using either catalyst, the phenolic hydroxy group attacks the aldehyde to form a hemiacetal which loses water and results in the benzofuran ester (6).

Table II below provides the analytical data for six benzofuran-7-carboxylic acid esters produced by Reaction Scheme I.

TABLE II

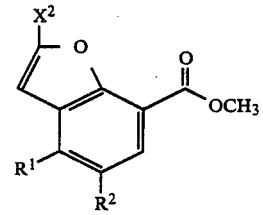

| Compounds | $R^1$ | $R^2$ | $X^2$ | Cyclization Catalysts | Chromatographic solvent | Recryst. solvent | Yield (%) | mp (°C.) | Analytical Analysis* |
|---|---|---|---|---|---|---|---|---|---|
| 6a | H | H | H | Amberlyst XN1010 | Hexane (100%) to EtOAc/ hexane(7.5/100) | — | 50.7 | liquid | $C_{10}H_8O$ |
| 6b | H | Br | H | Amberlyst XN1010 | Hexane $CH_2Cl_2$ (1/1 to 1/3) | — | 62.4 | 156–158 | $C_{10}H_7BrO_3$ |
| 6c | H | Cl | H | Amberlyst XN1010 | $CH_2Cl_2$ | $CH_2Cl_2$/ hexane | 21.0 | 144–145 | $C_{10}H_7ClO_3$ |
|  |  |  |  | TFA/reflux | $CH_2Cl_2$ | — | 63.2 |  |  |
| 6d | H | F | H | TFA/rt | $CH_2Cl_2$ | $Et_2O$/ hexane | 57.8 | 100–102 | $C_{10}H_7FO_3$ |
| 6f | Cl | H | H | TFA/rt | $CH_2Cl_2$ | — | 32.3 | 105–106 | $C_{10}H_7ClO_3$ |
| 6h | H | H | $CH_3$ | Amberlyst XN1010 | EtOAc/ hexane(1/9) | — | 54.0 | liquid | $C_{11}H_{10}O_3$ |

*Actual values for elemental combustion analysis were within 0.4% of calculated values. Nitrogen containing compounds were analyzed for C, H, N; others for C, H only.

The ester (6) can be easily converted to the acid (7) and from the acid (7) to the acid chloride (8). Reaction of acid chloride (8) with an amine such as 2-aminomethyl-1-ethylpyrrolidine as illustrated provides the 7-carboxamide (9) without difficulty.

Table III below summarizes the analytical data for six benzo[b]furan-7-carboxamides in accordance with the present invention produced by Reaction Scheme I.

TABLE III

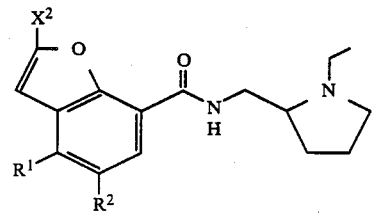

| Compounds | $R^1$ | $R^2$ | $X^2$ | Salt | Recryst Solvent | Yield (%) | mp (°C.) | Analytical Analysis* |
|---|---|---|---|---|---|---|---|---|
| 9a | H | H | H | 1.5 $C_4H_4O_4$** | 2-butanone | 38.9 | 131–132.5 | $C_{16}H_{20}N_2O_2$ .1.5 $C_4H_4O_4$ |

TABLE III-continued

| Compounds | $R^1$ | $R^2$ | $X^2$ | Salt | Recryst Solvent | Yield (%) | mp (°C.) | Analytical Analysis* |
|---|---|---|---|---|---|---|---|---|
| 9b | H | Br | H | — | EtOAc/hexane | 49.7 | 81–83 | $C_{16}H_{19}BrN_2O_2$ |
| 9c | H | Cl | H | 0.5 $C_4H_4O_4$ | 2-butanone | 44.3 | 158–159 | $C_{16}H_{19}ClN_2O_2$ .0.5 $C_4H_4O_4$ |
|  |  |  |  | $C_4H_4O_4$ | 2-butanone | 64.9 | 126.5–128.5 | $C_{16}H_{19}ClN_2O_2$ $C_4H_4O_4$ |
| 9d | H | F | H | $C_4H_4O_4$ | 2-butanone | 64.6 | 140–142 | $C_{16}H_{19}FN_2O_2$ .$C_4H_4O_4$ |
| 9f | Cl | H | H | 1.25 $C_4H_4O_4$ | 2-butanone | 30.4 | 115–118 | $C_{16}H_{19}ClN_2O_2$ 1.25 $C_4H_4O_4$ |
| 9h | H | H | $CH_3$ | — | — | 51.1 | liquid | $C_{17}H_{22}N_2O_2$ |

*Actual values for elemental combustion analysis were within 0.4% of calculated values. Nitrogen containing compounds were analyzed for C, H, N; others for C, H only.
**$C_4H_4O_4$ = fumarate Reaction Scheme I above is illustrated in more detail in Synthesis Example 1 below by reference to the synthesis of 5-chloro-N-(1-ethyl-2-pyrrolidinylmethyl)benzo[b]furan-7-carboxamide (Compound 9c).

Reaction Schemes II–IV below are syntheses for dihydrobenzo[b]furan-7-carboxamides.

Reaction Scheme II which is particularly useful in synthesizing the 2-alkyl-2,3-dihydrobenzo[b]furan derivatives proceeds from the Claisen rearrangement product (4) of Reaction Scheme I as follows:

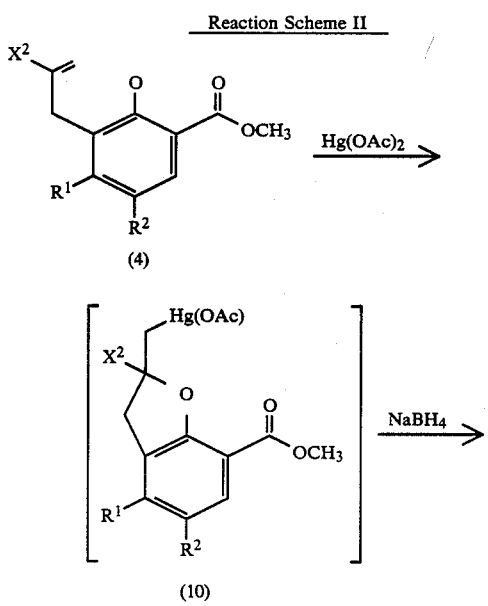

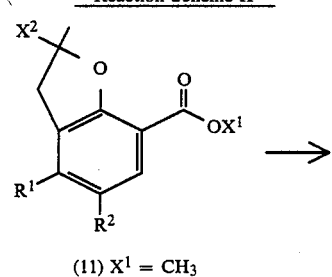

(11) $X^1 = CH_3$
(12) $X^1 = H$

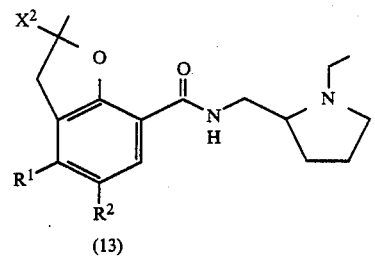

The intermediate (10) is obtained by reacting the product (4) with mercuric acetate in dry THF in the dark.

Reduction of intermediate (10) with sodium borohydride in 3N NaOH gives, upon workup by column chromatography, the dihydrobenzo[b]furan-7-carboxylic ester (11). The ester can be converted to the corresponding acid chloride and reacted with an appropriate amine to give dihydrobenzo[b]furans such as compound (13) as previously outlined. Table IV below provides the analytical data for dihydrobenzo[b]furan esters (11) obtained by Reaction Scheme II.

TABLE IV

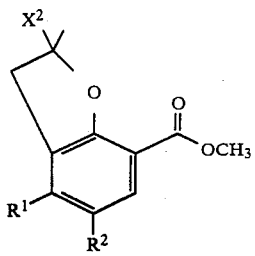

| Compounds | R¹ | R² | X² | Chromatographic solvent | Recryst. solvent | Yield (%) | mp (°C.) | Analytical Analysis* |
|---|---|---|---|---|---|---|---|---|
| 11a | H | H | H | EtOAc/hexane (0/100 to 20/100) | — | 54.0 | oil | $C_{11}H_{12}O_3$ |
| 11b | H | Br | H | EtOAc/hexane (0/100 to 25/100) | Hexane | 47.2 | 67–68 | $C_{11}H_{11}BrO_3$ |
| 11e | H | OCH₃ | H | — | Hexane | 68.3 | 75–77 | $C_{12}H_{14}O_4$ |
| 11f | Cl | H | H | — | Hexane | 71.9 | 77–80 | $C_{11}H_{11}ClO_3$ |
| 11g | OCH₃ | H | H | CH₂Cl₂ | — | 63.2 | 65.5–68.5 | $C_{12}H_{14}O_3$ |
| 11h | H | H | CH₃ | EtOAc/hexane (0/100 to 10/100) | — | 53.0 | oil | $C_{12}H_{14}O_3$ |

*Actual values for elemental combustion analysis were within 0.4% of calculated values. Nitrogen containing compounds were analyzed for C, H, N; others for C, H only.

TABLE V

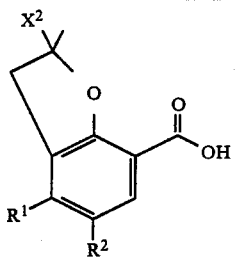

| Compounds | R¹ | R² | X² | Reaction Conditions | Recryst. Solvent | Yield (%) | mp (°C.) |
|---|---|---|---|---|---|---|---|
| 12a | H | H | H | 10% NaOH | — | 96.5 | oil |
| 12b | H | Br | H | KOH/CH₃OH/H₂O | — | 95.3 | 206–209 |
| 12e | H | OCH₃ | H | " | — | 95.6 | 122–124 |
| 12f | Cl | H | H | " | — | 99.0 | 210–213 |
| 12g | OCH₃ | H | H | " | — | 96.5 | 209–211 |
| 12i | Cl | Cl | H | SO₂Cl₂ | EtOAc | 54.3 | 204–207 |
| 12j | Cl | NO₂ | H | HNO₃/TFA | EtOAc | 34.8 | 193–197 |

TABLE VI

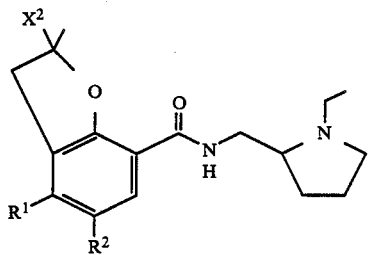

| Compounds | R¹ | R² | X² | Methods | Salts | Recryst. Solvent | Yield (%) | mp (°C.) | Analytical Analysis* |
|---|---|---|---|---|---|---|---|---|---|
| 13a | H | H | H | A | — | — | 76.5 | oil | $C_{17}H_{24}N_2O_2$ |
| 13b | H | Br | H | B | HCl | CH₂Cl₂/hexane | 53.2 | 168–170 | $C_{17}H_{23}BrN_2O_2 \cdot HCl$ |
| 13e | H | OCH₃ | H | B | $C_4H_4O_4$** | — | 62.8 | 143.5–145 | $C_{18}H_{26}N_2O_3 \cdot C_4H_4O_4$ |
| 13f | Cl | H | H | A | $C_4H_4O_4$ | 2-butanone | 45.2 | 163–164.5 | $C_{17}H_{23}ClN_2O_2 \cdot C_4H_4O_4$ |
| 13g | OCH₃ | H | H | A | $C_4H_4O_4$ | 2-butanone | 33.3 | 144–147 | $C_{18}H_{26}N_2O_3 \cdot C_4H_4O_4$ |

TABLE VI-continued

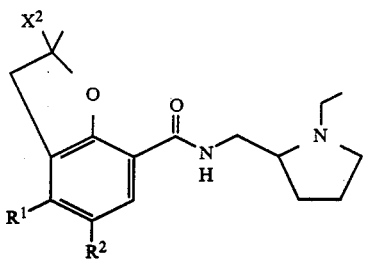

| Compounds | R¹ | R² | X² | Methods | Salts | Recryst. Solvent | Yield (%) | mp (°C.) | Analytical Analysis* |
|---|---|---|---|---|---|---|---|---|---|
| 13h | H | H | CH₃ | B | C₄H₄O₄ | EtOH/ acetone | 42.3 | 158-160 | $C_{18}H_{26}N_2O_2 \cdot C_4H_4O_4$ |
| 13i | Cl | Cl | H | A | C₄H₄O₄ | 2-butanone | 37.3 | 157-159 | $C_{17}H_{22}ClN_2O_2 \cdot C_4H_4O_4$ |
| 13j | Cl | NO₂ | H | A | — | — | 87.9 | solid | $C_{17}H_{22}ClN_3O_4$ |
| 13k | Cl | NH₂ | H | Pd/C | C₄H₄O₄ | acetone | 31.2 | 165-168 | $C_{17}H_{24}ClN_3O_2 \cdot C_4H_4O_4$ |

Actual values for elemental combustion analysis were within 0.4% of calculated values. Nitrogen containing compounds were analyzed for C, H, N; others for C, H only.

C₄H₄O₄ = fumarate

Substituents can be introduced into the benzene ring by selecting the appropriate substituted salicylic acid as a starting material or by reacting the benzofuran carboxylic acid with the appropriate electrophilic reagent. For example, chlorination of the 4-chloro derivative (12f) with sulfuryl chloride at room temperature furnishes the 4,5-dichloro derivative (12i) (Table V) in 54% yield. Nitration of compound (12f) in refluxing HNO₃/TFA gives the 4-chloro-5-nitro derivative (12j) in moderate yield. In general it is desired to perform the electrophilic substitutions before condensing the amine. Other modifications can be performed after condensation and are discussed below.

Table V below provides the reaction conditions for hydrolysis/substitution of the esters (11) with the yield and melting point for seven dihydrobenzofuran-7-carboxylic acid derivatives produced by following Reaction Scheme II. The carboxamides (13) are prepared by reaction of the acid chlorides or the esters (11) by heating with the appropriate amine, which in the case of compound (13) is 2-aminomethyl-1-ethylpyrrolidine. In most cases, the carboxamides are most conveniently isolated as their fumarate salts.

Reaction Scheme II is illustrated in more detail in Synthesis Example 2 for the synthesis of 4-chloro-N-(1-ethyl-2-pyrrolidinylmethyl)-2-methyl-2,3-dihydrobenzo[b]-furan-7-carboxamide fumarate (compound 13f). Table VI below summarizes the analytical data of several dihydrobenzofuran-7-carboxamides in accordance with the present invention.

2,3-Dihydrobenzo[b]furan-7-carboxylic acids (15) can be prepared according to Reaction Scheme III by lithiation of 2,3-dihydrobenzo[b]furan (14) with n-butyl lithium in TMEDA/hexane at room temperature, followed by quenching with dry ice and acidifying with concentrated HCl.

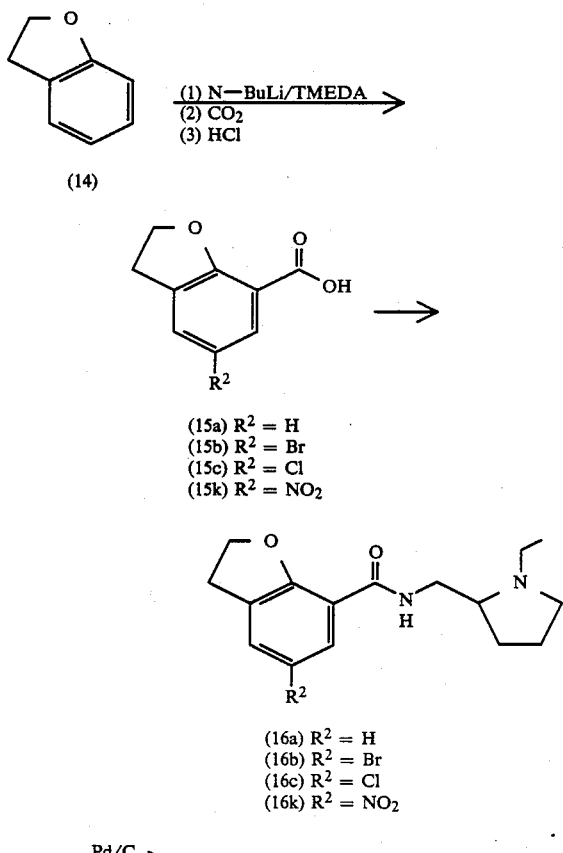

Reaction Scheme III

-continued
Reaction Scheme III

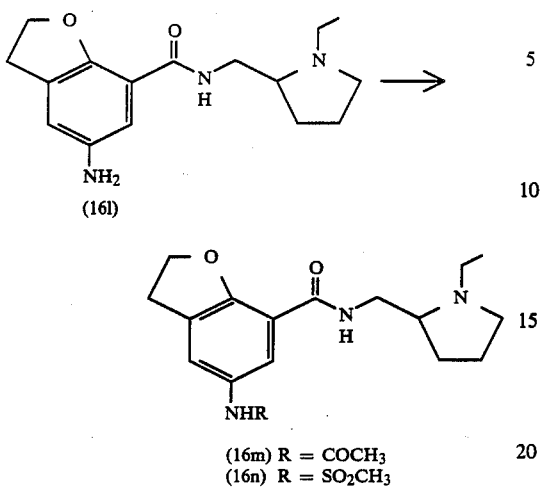

(16m) R = COCH$_3$
(16n) R = SO$_2$CH$_3$

The acid (15a) serves as a starting material for other 5-substituted derivatives. Bromination of (15a) with bromine in acetic acid containing a trace amount of iron yields the 5-bromo derivative (15b). Chlorination of (15a) with sulfuryl chloride at room temperature affords the 5-chloro derivative (15c). Nitration of (15a) carried out in either HNO$_3$/TFA at 0° C. to room temperature or HNO$_3$ in acetic acid at 70° C. yields the 5-nitro derivative (15k).

Other modifications can be performed after condensation with the amine. In particular, the 5-nitro derivative can be catalytically reduced to produce the 5-amino derivative. Acetylation or sulfonylation of the 5-amino compound produces the corresponding acylamide and sulfonamide. These compounds together with their melting point and analytical data are shown in Table VII below. The reactions are illustrated in Synthesis Examples 5, 6 and 7 below.

Dihydrobenzofuran-7-carboxamides can also be obtained through the following Reaction Scheme IV from 2,6-dibromophenols.

Reaction Scheme IV

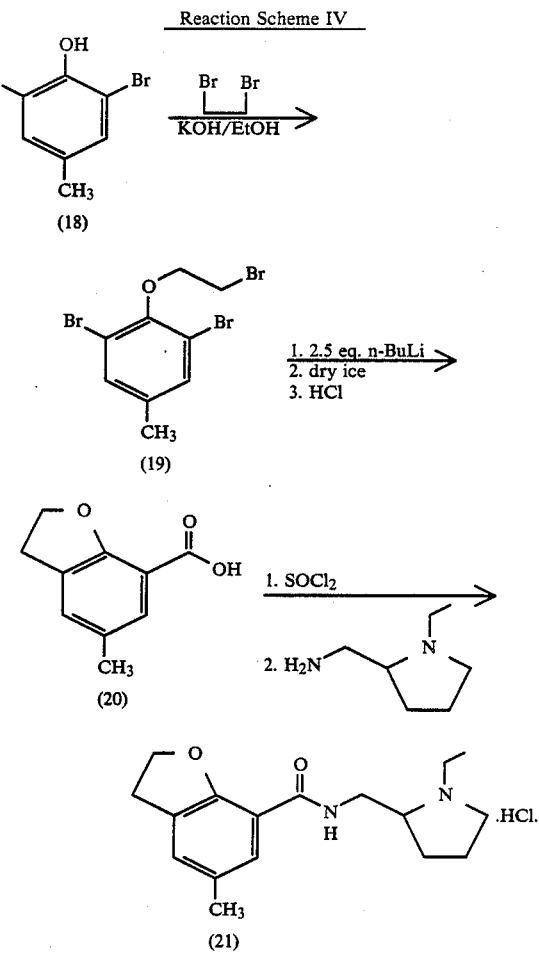

TABLE VII

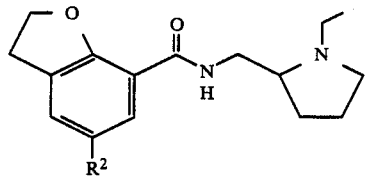

| Compounds | R$^2$ | Salts | Recryst. Solvents | Yield (%) | mp (°C.) | Analytical Analysis* |
|---|---|---|---|---|---|---|
| 16a | H | 1.5C$_4$H$_4$O$_4$** | 2-butanone | 49.7 | 151–152.5 | C$_{16}$H$_{22}$N$_2$O$_2$.1.5C$_4$H$_4$O$_4$ |
| 16b | Br | C$_4$H$_4$O$_4$ | 2-butanone | 41.1 | 160–161.5 | C$_{16}$H$_{21}$BrN$_2$O$_2$.C$_4$H$_4$O$_4$ |
| 16c | Cl | 1.5C$_4$H$_4$O$_4$ | 2-butanone | 42.9 | 149–150 | C$_{16}$H$_{21}$ClN$_2$O$_2$.1.5C$_4$H$_4$—O$_4$ |
| 16k | NO$_2$ | HCl | 2-butanone | 56.2 | 206.5–208.5 | C$_{16}$H$_{21}$N$_3$O$_4$.HCl |
| 16l | NH$_2$ | C$_4$H$_4$O$_4$.0.5H$_2$O | 2-butanone | 41.4 | 98–101 | C$_{16}$H$_{23}$N$_3$O$_2$.C$_4$H$_4$O$_4$.—0.5H$_2$O |
| 16m | NHCOCH$_3$ | C$_4$H$_4$O$_4$ | EtOH | 63.4 | 179–181 | C$_{18}$H$_{25}$N$_3$O$_3$.C$_4$H$_4$O$_4$ |
| 16n | NHSO$_2$—CH$_3$ | — | EtOH | 74.6 | 180–182 | C$_{17}$H$_{25}$N$_3$O$_4$S |

*Actual values for elemental combustion analysis were within 0.4% of calculated values. Nitrogen containing compounds were analyzed for C, H, N; others for C, H only.
**C$_4$H$_4$O$_4$ = fumarate Reaction Scheme III is illustrated in more detail by reference to the synthesis of 2,3-dihydrobenzo[b]furan-7-carboxylic acid (15a) and the 5-bromo and 5-nitro derivatives thereof in Synthesis Example 3 below.

Reaction Scheme IV proceeds via alkylation of a 2,6-dibromophenol (18) by reaction with 1,2-dibromoethane to provide the phenyloxyethyl bromide (19). By lithiating the bromide (19) using n-butyl lithium, quenching in dry ice and acidifying 2,3-dihydrobenzo[b]furan-7-carboxylic acid (20) is obtained. This acid is then converted to the acid chloride and this is reacted with the appropriate amine to give the carboxamide.

Reaction Scheme IV is illustrated in more detail in Synthesis Example 4 below wherein 5-methyl-N-(1-ethyl-2-pyrrolidinylmethyl)-2,3-dihydrobenzo[b]furan-7-carboxamide hydrochloride (21) is prepared by this reaction route.

Reaction Scheme IV is also useful in preparing carboxamides in which the condensed oxygen-containing ring contains 6 or 7 members by reacting 1,3-dibromopropane and 1,4-dibromobutane instead of the 1,2-dibromoethane. These rings can be dehydrogenated to form unsaturated derivatives by reacting the carboxylic acid ester with a dehydrogenation agent such as DDQ (2,3-dichloro-5,6-dicyano-1,4-benzoquinone).

A particularly advantageous carboxamide is prepared from 4-amino-5-chloro-2,3-dihydrobenzo[b]furan-7-carboxylic acid. This carboxylic acid is obtained by the following Reaction Scheme V:

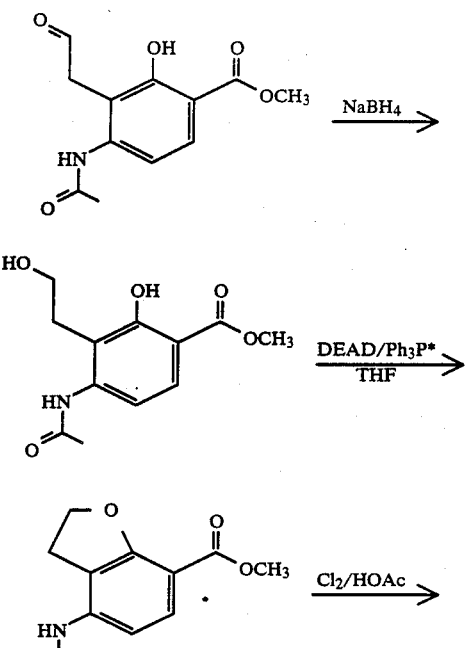

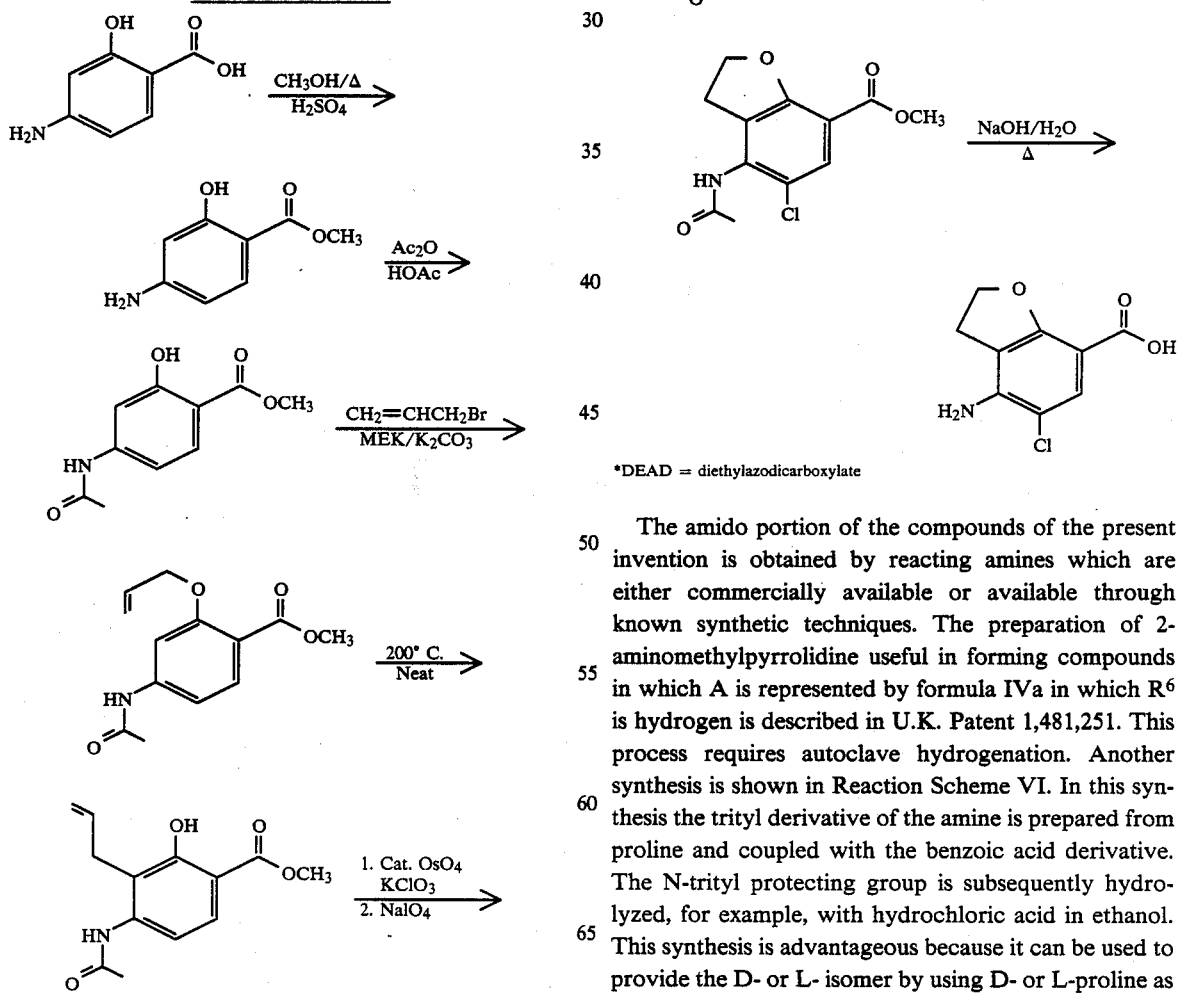

*DEAD = diethylazodicarboxylate

The amido portion of the compounds of the present invention is obtained by reacting amines which are either commercially available or available through known synthetic techniques. The preparation of 2-aminomethylpyrrolidine useful in forming compounds in which A is represented by formula IVa in which $R^6$ is hydrogen is described in U.K. Patent 1,481,251. This process requires autoclave hydrogenation. Another synthesis is shown in Reaction Scheme VI. In this synthesis the trityl derivative of the amine is prepared from proline and coupled with the benzoic acid derivative. The N-trityl protecting group is subsequently hydrolyzed, for example, with hydrochloric acid in ethanol. This synthesis is advantageous because it can be used to provide the D- or L- isomer by using D- or L-proline as a starting material.

Reaction Scheme VI

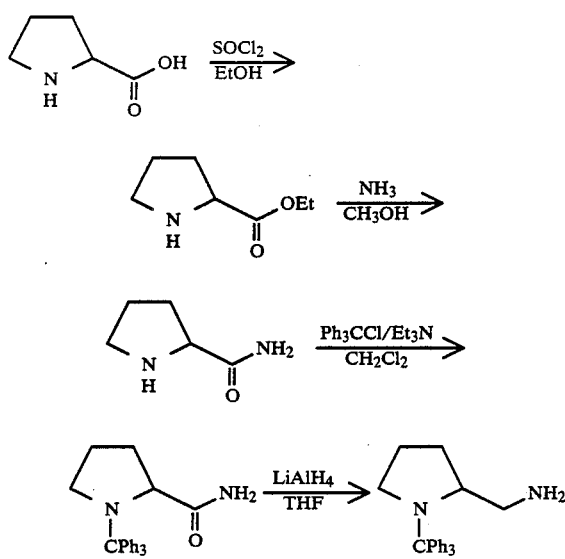

The preparation of amines corresponding to formula (VIII) is described in U.S. Pat. Nos. 4,207,327 and 4,309,552. Where $R^6$ is a propargyl group, as in Formula (IVa), the amine can be obtained by Reaction Scheme VII:

Reaction Scheme VII

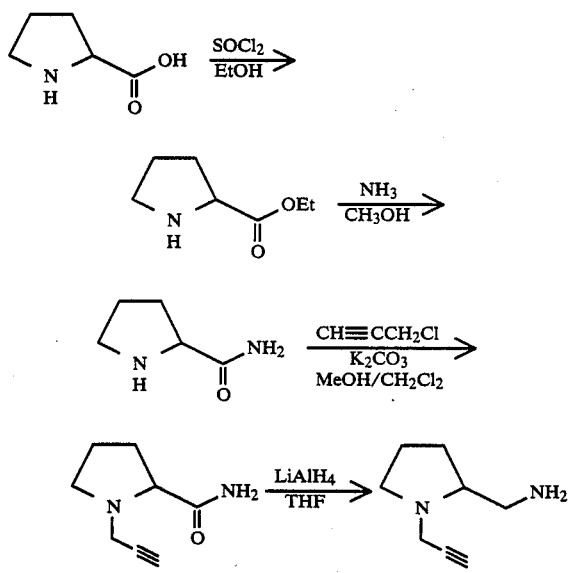

when A is represented by the formula (X), the compounds can be prepared by condensing a benzo[b]furan-7-carboxylic acid or dihydrobenzo[b]furan-7-carboxylic acid, acid chloride, or ester with 3-aminoquinuclidine in a manner similar to the synthesis described in European Patent Application No. 158,532. The acid, acid chloride or ester may be substituted on the benzofuran nucleus as provided in formula (I) above.

Hereinbelow the foregoing Syntheses are illustrated in more detail by the following non-limiting Synthesis Examples.

Synthesis Example 1 a. Methyl 5-chloro-2-hydroxybenzoate (2c)

A mixture of 5-chloro-2-hydroxybenzoic acid (100 g, 0.57 mol), 20 ml of conc. $H_2SO_4$ and 200 ml of dry methanol was heated under reflux for 22 hours. An additional 5 ml of conc. $H_2SO_4$ was then added and the solution heated for an additional 24 hours. The solvent was evaporated under reduced pressure and the resulting residue poured into aqueous saturated $Na_2CO_3$ and then extracted with $CH_2Cl_2$ (2×400 ml). The organic layers were combined, dried over anhydrous $Na_2SO_4$, and evaporated to give the desired compound as a white solid (100.5 g, 94.8% yield), mp 44°–46° C. IR (nujol) 1680 (ester) $cm^{-1}$. NMR ($CDCl_3$) δ 10.60 (s, 1H, OH), 7.73 (d, 1H, $J_{BC}$=3 Hz $H_C$), 7.33 (d of d, 1H, $J_{AB}$=9 Hz, $H_B$), 6.87 (d, 1H, $H_A$), and 3.92 (s, 3H, $CH_3$).

b. Preparation of methyl 2-allyloxy-5-chlorobenzoate (3c)

A mixture of methyl 5-chloro-2-hydroxybenzoate (2c) (45.0 g, 0.24 mol), allyl bromide (62.6 ml, 0.75 mol) and ground potassium carbonate (66.67 g, 0.48 mol) in 750 ml of dry acetone was heated under reflux for 2½ hours. The inorganic salt was removed by filtration, and the solvent and excess allyl bromide in the filtrate was evaporated to dryness to yield compound 3c quantitatively as a white solid, mp 25°–26° C. IR (nujol) 1738 (ester) $cm^{-1}$. NMR ($CDCl_3$) δ 7.63 (d, 1H, $J_{BC}$=3 Hz, $H_C$), 7.27 (d of d, 1H, $J_{AB}$=9 Hz, $H_B$), 6.77 (d. 1H, $H_A$), 6.30–6.47 (m, 3H, olefinic protons) and 3.87 (s, 3H, $CH_3$).

c. Preparation of methyl 5-chloro-2-hydroxy3-(2-propenyl)benzoate (4c)

Methyl 2-allyloxy-5-chlorobenzoate (3c) (76.66 g, 0.34 mol) was heated at 200° C. without solvent under argon for 20 hours. The dark brown liquid was distilled to give 67.9 g (88.5%) of product 4c as a clear liquid, b.p. 130°–136° C. (3.4 torr). IR (neat) 1675 (ester) $cm^{-1}$. NMR ($CDCl_3$) δ 10.50 (s, 1H, OH), 7.20 (d, 1H, J=3 Hz, aromatic proton), 7.13 (d, 1H, aromatic proton), 6.23–4.80 (m, 3H, olefinic protons), 3.90 (s, 3H, $CH_3$), and 3.32 (d, 2H, J=6 Hz, $CH_2$).

d. Preparation of 3-carbomethoxy-5-chloro2-hydroxy-phenylacetaldehyde (5c)

Osmium tetroxide (1.0 g, 3.9 mmol) was added to a mixture of methyl 5-chloro-2-hydroxy-3-(2-propenyl)-benzoate (4c) (22.7 g, 0.1 mol), ether (400 ml), and water (400 ml). After stirring at room temperature for 5 minutes, sodium periodate (47.06 g, 0.22 mol) was added in portions. The mixture was stirred at room temperature for another 21 hours, and then poured into 800 ml of water. The layers were separated and the aqueous layer extracted with ethyl ether (2×400 ml). The organic layers were combined, dried over anhydrous $Na_2SO_4$ and then filtered through a column of Florisil (85 g) to remove inorganic impurity. Evaporation of the ether yielded 5c quantitatively as a brown solid, m.p. 49°–59° C., which appeared hygroscopic. The crude product was used for the next reaction without purification. NMR ($CDCl_3$) δ 10.90 (s, 1H, OH), 9.67 (t, 1H, J=1.5 Hz, CHO), 7.70 (d, 1H, J=3 Hz, aromatic proton), 7.23 (d, 1H, aromatic proton), 3.97 (s, 3H, $CH_3$) and 3.70 (d, 2H, $CH_2$).

e. Preparation of 7-carbomethoxy-5-chlorobenzo[b]furan (6c)

A trifluoroacetic acid (25 ml) solution of 3-carbomethoxy-5-chloro-2-hydroxyphenylacetaldehyde (5c) (5.20 g, 22.7 mmol) was refluxed for 2 hours under argon, and then poured into saturated $Na_2CO_3$. The resulting precipitate was collected by filtration, and then purified by column chromatography (100% $CH_2Cl_2$) to give 6c as a cream colored solid (3.02 g, 63.2% yield). Analytical sample was prepared by recrystallization from ethyl ether, mp 144°–145° C. IR (nujol) 1710 (ester) $cm^{-1}$. NMR ($CDCl_3$) δ 7.87–6.70 (m, 4H, aromatic protons) and 4.0 (s, 3H, $CH_3$).

Anal. Calcd for $C_{10}H_7ClO_3$: C, 57.03; H, 3.35. Found: C, 57.03, H, 3.48.

f. Preparation of 5-chlorobenzo[b]furan-7-carboxylic acid (7c)

A solution of 7-carbomethoxy-5-chlorobenzo[b]furan (6c) (3.02 g, 14.3 mmol) containing potassium hydroxide (3.22 g) in 100 ml of aqueous methanol ($CH_3OH/H_2O$=3/2) was stirred at room temperature overnight. The mixture was concentrated under reduced pressure. The residue was acidified with conc. HCl to pH of about 1, cooled in freezer for several hours and filtered to give 7c as an off-white solid (2.65 g, 94.3%), mp 212°–215° C. NMR (DMSO-$d_6$) δ 8.0–6.87 (m, 5H, aromatic protons and OH).

g. Preparation of 5-chloro-N-(1-ethyl-2-pyrrolidinylmethyl)benzo[b]furan-7-carboxamide fumarate (9c)

A mixture of 5-chlorobenzo[b]furan-7-carboxylic acid (7c) (4.41 g, 22.4 mmol) and thionyl chloride (6.5 ml, 89.1 mmol) in 90 ml of toluene was heated under reflux for 2½ hours. The solvent and excess thionyl chloride were removed under reduced pressure to give the corresponding 7-carboxylic acid chloride (8c) as a yellow solid. The acid chloride was then dissolved in 90 ml of methylene chloride and cooled to 0° C. with an ice bath. To this solution was added dropwise 2-aminomethyl-1-ethylpyrrolidine (2.88 g, 22.4 mmol) in 20 ml of methylene chloride. The yellow solution was stirred at ambient temperature overnight, and then poured into 90 ml of 10% NaOH. The layers were separated, and the organic layer dried over anhydrous $Na_2SO_4$ and evaporated to give the desired product 9c as its free base (6.46 g, 94.0% yield). The carboxamide is conveniently isolated as its fumarate by adding to the free base in 100 ml of absolute ethanol 1 equivalent of fumaric acid. After stirring at room temperature for 1 hour, the solution was reduced to a small volume, this was triturated with acetone, cooled in the freezer briefly, and the solid collected on a filter to give 9c as an off-white solid (7.64 g, 80.7%). The analytical sample was prepared by recrystallization from 2-butanone, mp 126.5°–128.5° C. NMR (DMSO-$d_6$) δ8.70 (br s, 1H, exchangeable with $D_2O$, NH), 8.0 (d, 1H, J=2 Hz, aromatic proton), 7.77 (d, 1H, aromatic proton), 7.57 (d, 1H, aromatic proton) 7.20 (br s, exchangeable with $D_2O$, 2 COOH), 6.93 (d, 1H, aromatic proton), 6.47 (2, 2H, 2CH), 3.70–1.60 (m, 11H, 5$CH_2$ and CHN), and 1.20 (t, 3H, J=7 Hz, $CH_3$).

Anal. Calcd for $C_{16}H_{19}ClN_2O_2 \cdot C_4H_4O_4$: C, 56.81; H, 5.48; N, 6.62. Found: C, 57.11; H, 5.52; N, 6.52.

Synthesis Example 2 a. Preparation of methyl 4-chloro-2-hydroxybenzoate (2f)

A mixture of 4-chloro-2-hydroxybenzoic acid (200 g, 1.16 mol) and 40 ml conc. sulfuric acid in 400 ml of methanol was heated under reflux for 20 ½ hours. The solvent was evaporated under reduced pressure, the residue poured into aqueous saturated $Na_2CO_3$, and then extracted with ethyl ether (3×500 ml). The combined organic layers were dried over anhydrous $Na_2SO_4$, and evaporated to give 2f (191.6 g, 88.6% yield) as an oil. This was used for the next reaction without purification. IR (neat) 3150 (OH), 1728 (C=O), and 1678 (C=O) $cm^{-1}$. NMR ($CDCl_3$) δ 10.27 (br s, 1H, OH), 7.47 (d, 1H, $J_{BC}$=8 Hz, $H_C$), 6.80 (d, 1H, $J_{AB}$=2 Hz, $H_A$), 6.63 (d of d, 1H, $H_B$), and 3.85 (s, 3H, $CH_3$).

b. Preparation of methyl 2-allyloxy-4-chlorobenzoate (3f)

A mixture of methyl 4-chloro-2-hydroxybenzoate (2f) (96.3 g, 0.52 mol), allyl bromide (134 ml, 1.55 mol) and ground potassium carbonate (107 g, 0.77 mol) in 1500 ml of dry acetone was heated under reflux for 20 hours. The inorganic salt was removed by filtration, and the solvent and excess allyl bromide evaporated to dryness to give 3f (117 g, 99.6% yield) as a yellow solid, mp 47°–55° C. NMR ($CDCl_3$) δ 7.73 (d, 1H, J=8 Hz, aromatic proton meta to Cl), 6.97 (m, 2H, aromatic protons alpha to Cl), 6.40–5.17 (m, 3H, olefinic protons), 4.57 (m, 2H, $CH_2$) and 3.90 (s, 3H, $CH_3$).

c. Preparation of methyl 4-chloro-2-hydroxy-3-(2-propenyl)benzoate (4f)

A solution of methyl 2-allyloxy-4-chlorobenzoate (3f) (50.6 g, 0.22 mol) in 100 ml of N,N-dimethylaniline was heated under argon in an oil bath at 190°–205° C. for 20 hours. The solvent was removed by distillation and the residue purified by column chromatography (silica gel, $CH_2Cl_2$/hexane) to give 4f (36.0 g, 71.1% yield) as a very light oil. IR (nujol) 1665 (C=O) $cm^{-1}$. NMR ($CDCl_3$) δ 11.23 (s, 1H, OH), 7.47 (d, 1H, J=9 Hz, aromatic proton meta to Cl), 6.77 (d, 1H, aromatic proton alpha to Cl), 6.17–4.77 (m, 3H, olefinic protons), 3.87 (s, 3H, $CH_3$) and 3.50 (m, 2H, $CH_2$).

d. Preparation of 7-carbomethoxy-4-chloro-2-methyl-2,3-dihydrobenzo[b]furan (11f)

A solution of methyl 4-chloro-2-hydroxy-3-(2-propenyl)benzoate (4f) (4.17 g, 18.4 mmol) and mercuric acetate (5.86 g, 18.4 mmol) in 60 ml of THF was heated under reflux for 3 hours, and then cooled to room temperature. To this was added dropwise at 0° C. a solution of 0.70 g (18.4 mmol) sodium borohydride in 4.2 ml of 3N NaOH. When the addition was complete, the mixture was stirred at ambient temperature for an additional 2 hours. and then treated with 55 ml saturated $Na_2CO_3$. The precipitated mercury was removed by filtration with the aid of Celite. The organic layer was separated, dried over anhydrous $Na_2SO_4$ and evaporated to give a mixture of product 11f and starting material (4f) (total 3.89 g). The product 11f was isolated by recrystallization from hexane to afford 3.0 g (71.9% yield) of white solid, mp 77°–80° C. IR (KBr) 1685 (C=O) $cm^{-1}$. NMR ($CDCl_3$) δ 7.50 (d, 1H, J=8 Hz, aromatic proton meta to Cl), 6.67 (d, 1H, aromatic proton alpha to Cl), 5.03 (m, 1H, CH), 3.83 (s, 3H, OCH₃) 3.03 (m, 2H, CH₂) and 1.52 (d, 3H, J=6 Hz, CH₃).

Anal. Calcd for $C_{11}H_{11}ClO_3$: C, 58.29; H, 4.89. Found: C, 58.27; H, 4.99.

e. Preparation of 4-chloro-2-methyl-2,3-dihydrobenzo[b]furan-7-carboxylic acid (12f)

To a solution of 7-carbomethoxy-4-chloro-2-methyl-2,3-dihydrobenzo[b]furan (11f) (2.76 g, 12.2 mmol) in 48 ml of methanol there was added 3.0 g (53 mmole) of KOH in 32 ml of water. The solution was stirred at room temperature overnight, and then concentrated under reduced pressure. The residue was treated with 100 ml of water, and then acidified with conc. HCl to pH of about 1. The resulting white solid 12f was collected on a filter to yield 2.88 g (99.0%) of acid, mp 210°–213° C. IR (KBr) 1668 (C=O) cm⁻¹. NMR (DMSO-d₆) δ 7.63 (d, 1H, J=9 Hz, aromatic proton meta to Cl), 6.93 (d, 1H, aromatic proton alph to Cl), 5.13 (m, 2H, OH, and CH), 3.63–2.60 (m, 2H, CH₂) and 1.50 (d, 3H, J=6 Hz, CH₃).

f. Preparation of 4-chloro-N-(1-ethyl-2-pyrrolidinylmethyl)-2-methyl-2,3-dihydrobenzo[b]furan-7-carboxamide fumarate (13f)

A mixture of 4-chloro-2-methyl-2,3-dihydrobenzo[b]furan-7-carboxylic acid (12f) (2.42 g, 11.4 mmol) and thionyl chloride (4.2 ml, 57.0 mmol) in 30 ml of toluene was heated under reflux for 3 hours. The solvent and excess thionyl chloride were removed under reduced pressure to give the corresponding 7-carboxylic acid chloride as a cream colored solid. The acid chloride was then dissolved in 30 ml of CH₂Cl₂ and cooled to 0° C. in an ice bath. To this there was added dropwise 2-aminomethyl-1-ethylpyrrolidine (1.46 g, 11.4 mmol) in 5 ml of methylene chloride. The solution was stirred at ambient temperature overnight, and then poured into saturated Na₂CO₃. The organic layer was separated, dried over anhydrous Na₂SO₄ and evaporated to give the desired product as a brown oil (2.77 g). To a solution of the free base in 50 ml of absolute ethanol was added 1.0 g (8.6 mmol) of fumaric acid. The mixture was stirred at room temperature for 2 hours, and cooled in the freezer for 1 hour. The resulting precipitate was collected on a filter and the solid purified by recrystallization from 2-butanone to give 13f (2.26 g, 45.2% yield) as white crystals, mp 163°–164.5° C. IR (nujol) 3350 (NH), 1710 (CO₂H), and 1660 (CONH) cm⁻¹. NMR (DMSO-d₆) δ 8.20 (br s, 1H, NH), 7.63 (d, 1H, J=8 Hz, aromatic proton meta to Cl), 7.33 (br s, 2H, COOH), 6.97 (d, 1H, aromatic proton alpha to Cl), 6.57 (S, 2H, 2CH=), 5.17 (m, 1H, CHO), 3.77–1.63 (m, 12H, 6CH₂), 1.45 (d, 3H, J=6 Hz, CH₃CHO), and 1.13 (t, 3H, J=7 Hz, CH₂CH₃).

Anal. Calcd for $C_{17}H_{23}ClN_2O_2 \cdot C_4H_4O_4$: C, 57.47; H, 6.20; N, 6.38. Found: C, 57.62; H, 6.29; N, 6.22.

Synthesis Example 3 a. Preparation of 2,3-dihydrobenzo[b]furan-7-carboxylic acid (15a)

To a solution of n-BuLi (1.7 M, 123 ml, 0.21 mol) in 400 ml of hexane at room temperature was added 24.3 g (0.21 mol) of N,N,N′,N′-tetramethylethylenediamine (TMEDA), followed by a hexane (40 ml) solution of 2,3-dihydrobenzo[b]furan (14) (12.56 g, 0.11 mol). The mixture was stirred under argon at room temperature for 4 hours, and then poured into dry ice (pre-washing with anhydrous ether). After stirring at ambient temperature overnight, the mixture was diluted with water (300 ml), and the layers separated. The aqueous layer was acidified with conc. HCl to pH 1, cooled and the precipitate collected on a filter. This was recrystallized from CH₂Cl₂ to give 15a (9.43 g, 54.7%) as a white solid, mp 167°–169.5° C.

b. Preparation of 5-bromo-2,3-dihydrobenzo[b]furan-7-carboxylic acid (15b)

To an ice-cooled acetic acid solution (5 ml) of 2,3-dihydrobenzo[b]furan-7-carboxylic acid (15a) (0.33 g, 2.0 mmol) there was added iron (8 mg, 0.14 mmol) and bromine (0.32 g, 2.0 mmol) in 1 ml of acetic acid. The mixture was stirred at room temperature for 18 hours and then poured into water (20 ml). After cooling in the freezer for 1½ hours the product was collected on a filter, and recrystallized from ethyl acetate to give 0.24 g (50.3%) of 15b as a white crystalline solid, mp 228°–229° C.

c. Preparation of 5-nitro-2,3-dihydrobenzo[b]furan-7-carboxylic acid (15k)

Method A: To an ice-cooled solution of 2,3-dihydrobenzo[b]furan-7-carboxylic acid (15a) (0.33 g, 2.0 mmol) in 3 ml of TFA there was added dropwise 0.6 ml of HNO₃. At the end of 1 hour, the cooling bath was removed. After an additional 3 hours of stirring, the mixture was poured into ice-water. The precipitate was collected on a filter to give 0.22 g (52.6%) of crude 15k. This was recrystallized from ethyl acetate to provide 88 mg of acid 15k (21.4%), mp 249°–251.5° C.

Method B: To an ice-cooled solution of 2,3-dihydrobenzo[b]furan-7-carboxylic acid (15a) (0.33 g, 2.0 mmol) in 3 ml of acetic acid there was added dropwise 0.6 ml of HNO₃. The mixture was stirred in a warm oil bath (70° C.) for 24 hours, and then poured into water. After cooling, the product was collected on a filter to give 0.21 g of solid (50.2%). This was recrystallized from ethyl acetate to afford 0.14 g (33.5%) of 15k, mp 249°–251.5° C.

d. Preparation of N-(1-ethyl-2-pyrrolidinylmethyl)-5-nitro-2,3-dihydrobenzo[b]furan-7-carboxamide (16k)

A mixture of (15k) (3.0 mmol) and thionyl chloride (12.3 mmol) in 15 ml of toluene was heated under reflux for 3 hours. The solvent and excess of thionyl chloride was removed under reduced pressure to give the corresponding 7-carboxylic acid chloride. This was then dissolved in 15 ml methylene chloride and cooled to 0° C. in an ice bath. To this there was added dropwise 2-aminomethyl-1-ethylpyrrolidine (3.0 mmol) in 5 ml of methylene chloride. The yellow solution was stirred at ambient temperature overnight, and then taken to dryness in vacuum. The residue was recrystallized from 2-butanone to give 16k as a solid.

Synthesis Example 4 a. Preparation of 2-(2,6-dibromo-4-methylphenyloxy)ethyl bromide (19)

A mixture of 2,6-dibromo-4-methylphenol (18) (26.59 g, 0.1 mol), 1,2-dibromoethane (11.2 ml, 0.13 mol) and potassium hydroxide (8.42 g, 0.15 mol) in 200 ml of absolute ethanol was heated under reflux for 24 hours. The inorganic salt was collected on a filter and the filtrate taken to dryness. The resulting mixture was treated with ethyl ether, chilled, and the solid, which proved to be recovered phenol, collected on a filter. The filtrate was evaporated to afford the ether 19 (24.5 g, 65.7%) as a liquid. This was purified by distillation (0.5 torr, 120°–124° C.) to yield 19.79 g (53.0%) of product. NMR (CDCl$_3$) δ 7.25 (s, 2H, aromatic protons), 3.55–4.38 (m, 4H, 2CH$_2$), and 2.27 (s, 3H, CH$_3$).

b. Preparation of 5-methyl-2,3-dihydrobenzo[b]furan-7-carboxylic acid (20)

To a stirred solution of 2-(2,6-dibromo-4-methylphenyloxy)ethyl bromide (19) (5.82 g, 15.6 mmol) in dry THF (90 ml) and hexane (30 ml) under argon there was added 7.8 ml of n-BuLi (2.5M in hexane) at −78° C. (dry ice/acetone bath). After 30 minutes at −78° C., an additional 7.8 ml of n-BuLi was added. After an additional 1 hour stirring, the light yellow reaction solution was poured into a slurry of dry ice (prewashed with dry ether). After the mixture had come to room temperature, the precipitated white solid was collected on a filter, treated with 1N HCl to adjust the pH of the supernatant liquid to 1. The mixture was cooled briefly in the freezer, and the solid collected on a filter to afford 2.52 g (90.7%) of acid 20. The crude product was recrystallized from CH$_3$OH/H$_2$O to yield 1.70 g (61.2%) of 20 as a white solid, mp 177°–179° C. IR(KBr) 3420 (OH) and 1680(C=O) cm$^{-1}$. NMR(CDCl$_3$) δ 8.47 (br s, 1H, OH), 7.50 (s, 1H, aromatic proton), 7.15 (s, 1H, aromatic proton), 4.70 (t, 2H, J=9 Hz, OCH$_2$), 3.20 (t, 2H, OCH$_2$CH$_2$), and 2.32 (s, 3H, CH$_3$).

Anal. Calcd for C$_{10}$H$_{10}$O$_3$: C, 67.41; H, 5.66. Found: C, 67.45; H, 5.78.

c. Preparation of N-(1-ethyl-2-pyrrolidinylmethyl)-5-methyl-2,3-dihydrobenzo[b]furan-7-carboxamide hydrochloride (21)

A mixture of 2-methyl-2,3-dihydrobenzo[b]furan-7-carboxylic acid (20) (3.43 g, 19.25 mmol) and thionyl chloride (7.0 ml, 96.2 mmol) in 40 ml of toluene was heated under reflux for 3 hours. The solvent and excess of thionyl chloride were removed under reduced pressure to give the corresponding 7-carboxylic acid chloride. This was then dissolved in 25 ml of CH$_2$Cl$_2$ and cooled at 0° C. with an ice bath. To this there was added dropwise 2-aminomethyl-1-ethylpyrrolidine (2.47 g, 19.25 mmol) in 10 ml of CH$_2$Cl$_2$. The solution was stirred overnight at room temperature and then evaporated to dryness to afford crude carboxamide (6.24 g, 100%). This was purified by recrystallization from acetone to give 5.29 g (84.6%) as white crystals, mp 203.5°–205° C. IR (nujol) 3340 (NH), and 1645 (C=O) cm$^{-1}$. NMR (DMSO) δ 8.13 (br s, 1H, NH), 7.25 (s, 1H, aromatic proton), 7.10 (s, 1H, aromatic proton), 4.58 (t, 2H, J=9 Hz, OCH$_2$), 1.88 (s, 3H, CH$_3$), and 1.25 (t, 3H, J=7 Hz, CH$_2$CH$_3$).

Anal. Calcd for C$_{17}$H$_{24}$N$_2$O$_2$. HCl: C, 62.85; H, 7.76; N, 8.62. Found: C, 62.99; H, 7.79; N, 8.56.

Synthesis Example 5 a. Preparation of 5-amino-N-(1-ethyl-2-pyrrolidinylmethyl)-2,3-dihydrobenzo[b]furan-7-carboxamide fumarate (16l)

A mixture of N-(1-ethyl-2-pyrrolidinylmethyl)-5-nitro-2,3-dihydrobenzo[b]furan-7-carboxamide (16k) (1.08 g, 3.4 mmol) and palladium on carbon (5%) (0.10 g) in 25 ml of absolute ethanol was shaken under hydrogen for 18 hours. The catalyst was collected on a filter with the aid of Celite and the filtrate evaporated. The residue was purified by column chromatography (silica gel, NH$_4$OH/CH$_3$OH/CH$_2$Cl$_2$=0.1/1/100 to 0.1/6/100). The product was isolated as the fumarate and recrystallized from 2-butanone to afford 0.57 g (41.4%) of 16l as a yellow solid, mp 98°–101° C.

Synthesis Example 6 a. Preparation of 5-acetamido-N-(1-ethyl-2-pyrrolidinylmethyl)-2,3-dihydrobenzo[b]furan-7-carboxamide fumarate (16m)

A solution of 5-amino-N-(1-ethyl-2-pyrrolidinylmethyl)-2,3-dihydrobenzo[b]furan-7-carboxamide (16l) (1.02 g, 3.5 mmol) in 10 ml of acetic anhydride was stirred at room temperature overnight. The mixture was added to 50 ml of ethyl ether, cooled and the precipitate collected on a filter. This solid was dissolved in 50 ml of CH$_2$Cl$_2$, and washed with saturated NaHCO$_3$ (2×50 ml). The organic layer was dried over anhydrous Na$_2$SO$_4$, and evaporated to give the free base (1.03 g, 88.8%). The product was characterized as its fumarate; there was obtained 1.26 g of the salt (80.3%), mp 179°–181° C. (EtOH).

Synthesis Example 7 a. Preparation of N-(1-ethyl-2-pyrrolidinylmethyl)-5-methanesulfonamido-2,3-dihydrobenzo[b]furan-7-carboxamide (16n)

A solution of 5-amino-N-(1-ethyl-2-pyrrolidinylmethyl)-2,3-dihydrobenzo[b]furan-7-carboxamide (16l) (1.80 g, 6.2 mmol) and methanesulfonyl chloride (12.78 g, 0.11 mol) in 30 ml of methylene chloride was heated to reflux overnight. The solution was diluted with CH$_2$Cl$_2$ (30 ml), and then extracted with water (2×30 ml). The combined aqueous layers were made basic with NaHCO$_3$ powder, and extracted with CH$_2$Cl$_2$ (4×50 ml). The organic extracts were combined, dried over anhydrous Na$_2$SO$_4$, and evaporated to give crude 16n (2.5 g, 98.8%). This was recrystallized from EtOH/charcoal to afford 1.70 g of amide as a white solid, mp 180°–182° C.

Hereinabove the invention has been described by reference to the synthesis of pyrrolidinylmethyl derivatives by reacting benzo[b]furan-7-carboxylic or dihydrobenzo[b]furan-7-carboxylic acids or the corresponding esters or acid chlorides with 2-aminomethyl-1-ethylpyrrolidine. Other benzofuran carboxamides as defined in A in general formula (I) can be prepared in an analogous manner by reacting the aforementioned acids, esters or acid chlorides with other amines as shown in Synthesis Example 8 to 10 below.

Synthesis Example 8 a. Preparation of 5-bromobenzo[b]furan-7-carboxylic acid chloride

A mixture of 5-bromobenzo[b]furan-7-carboxylic acid (5.5 g, 22.8 mmol) and thionyl chloride (6.7 ml, 91.9 mmol) in 40 ml of toluene was heated under reflux for 3 hours. The solvent and excess thionyl chloride were then removed under reduced pressure to give 8b (5.04 g, 85.2%) as a yellow solid. This was used for subsequent reactions with amines without purification.

b. Preparation of 5-bromo-N-(2-diethylaminoethyl)benzo[b]-furan-7-carboxamide hydrochloride To an ice-cooled solution of 5-bromobenzo[b]furan-7-carboxylic acid chloride (1.5 g, 5.8 mmol) in 15 ml of $CH_2Cl_2$, there was added N,N-diethylethylenediamine (0.74 g, 6.4 mmol) in 10 ml of $CH_2Cl_2$. After stirring at ambient temperature overnight, the precipitate was collected on a filter to give the crude amide (1.14 g, 53.2%). This was recrystallized from ethanol (decolorization with charcoal) to give 0.54 g (24.8%) of the desired amide as a white solid, mp 202°–203.5° C. IR (KBr) 1675 (C=O) cm$^{-1}$.

Anal. Calcd for $C_{15}H_{19}BrN_2O_2 \cdot HCl$: C, 47.95; H, 5.37; N, 7.46. Found: C, 47.87; H. 5.48; N, 7.33.

Synthesis Example 9 a. Preparation of [exo]-5-bromo-N-[8-(phenylmethyl)-8-azabicyclo[3,2,-1]oct-3-yl]benzo[b]furan-7-carboxamide To an ice-cooled solution of 5-bromobenzo[b]furan -7-carboxylic acid chloride prepared as in Synthesis Example 8 (1.5 g, 5.8 mmol) in 15 ml of $CH_2Cl_2$, there was added 8-benzyl-3β-amino-1αH, 5αH-nortropane (1.25 g, 5.8 mmol) in 10 ml of $CH_2Cl_2$. The mixture was stirred at ambient temperature overnight and then poured into saturated aqueous $NaHCO_3$. The layers were separated, and the organic layer dried over anhydrous $Na_2SO_4$. Evaporation of solvent gave crude amide (2.28 g, 89.5%). The analytical sample was obtained by two recrystallizations from ethanol to give a sample of the target amide pure (0.81 g, 31.8%) as a white crystalline solid, mp 161°–163° C. IR (KBr) 1662 (C=O) cm$^{-1}$.

Anal. Calcd for $C_{23}H_{23}BrN_2O_2$: C, 62.88; H, 5.28; N, 6.38. Found: C, 62.99; H, 5.37; N, 6.27.

Synthesis Example 10 a. Preparation of N-(1-benzyl-3-pyrrolidinyl)-5-bromobenzo[b]furan-7-carboxamide fumarate To an ice-cooled solution of 5-bromobenzo[b]furan-7-carboxylic acid chloride prepared as in Synthesis Example 8 (1.82 g, 7.0 mmol) in 25 ml of $CH_2Cl_2$, there was added 3-amino-1-benzylpyrrolidine (1.24 g, 7.0 mmol) in 10 ml of $CH_2Cl_2$. The mixture was stirred at ambient temperature overnight, and then poured into saturated aqueous $NaHCO_3$. The layers were separated, and the organic layer dried over anhydrous $Na_2SO_4$. Evaporation of the solvent afforded the desired product as its free base (1.93 g, 68.9%). This was more conveniently isolated as its fumarate by adding to the free base in 15 ml of absolute ethanol 0.56 g of fumaric acid, and the mixture stirred at room temperature for 1 hour. The resulting precipitate was collected on a filter to give the salt (2.12 g, 58.6%). This was recrystallized from ethanol to furnish an analytically pure sample of the desired amide (1.10 g, 30.5%) as a beige solid, mp 197°–200° C. IR (KBr) 1710 (COOH), 1655 (CONH) cm$^{-1}$.

Anal. Calcd for $C_{20}H_{19}BrN_2O_2 \cdot C_4H_4O_4$: C, 55.93; H, 4.50; N, 5.44. Found: C, 56.44; H, 4.85; N, 5.81.

In Vivo Screening Tests a. Antipsychotic Screen

The effect of each of the benzofurancarboxamides shown in Table VIII below on apomorphine induced climbing behavior was tested under the conditions described by Costetin et al. "Rapid and Dissociated Changes in Sensitivities of Different Dopamine Receptors in Mouse Brain," *Nature*, 257, 405 (1975). Each mouse was administered from 0.1 to 50 mg/kg of test compound and antagonism was observed 20 minutes after injection of 1 mg/kg apomorphine induced climbing behavior. The ED 50 values are shown in Table VIII.

b. Antiemetic Screen

Each of the test compounds shown in Table VIII was administered subcutaneously to two Beagle dogs at dosage levels of 0.05, 0.1, 1.0 and 10.0 mg/kg. One hour following administration of the test compound, each animal received 0.1 mg/kg, sc, of apomorphine HCl. Apomorphine consistently evokes an immediate emetic response through direct dopaminergic interaction at the medullary chemoreceptor trigger zone (CTZ). Antiemetic compounds which act at the CTZ and/or the midbrain vomiting center will block this effect. If both animals receiving a particular treatment are protected, (i.e., no emetic response within one hour after apomorphine), the test compound is considered active. The dosage at which both animals were protected (100% effect) is shown in Table VIII.

TABLE VIII

Effects of Benzofuran/Dihydrobenzofuran Compounds In Vivo Screening Tests

| Structure | Apomorphine Emesis (Dog) 100% Effect Dosage level mg/kg, s.c. | Apomorphine Climbing (Mouse) Approx. 50% ED (mg/kg, s.c.) |
|---|---|---|
| R = H (benzofuran with R at top, N-ethylpyrrolidinylmethyl amide) | 10.0 | 12 (i.p.) |
| R = CH₃ | 10.0 | 3 (i.p.) |
| R = H (dihydrobenzofuran with R at bottom) | 1.0 | 20 (i.p.) |
| R = Cl | 1.0 | 15 (oral) |
|  |  | 5 (i.p.) |
| R = NO₂ | 1.0 | 20 (i.p.) |
|  |  | 15 (oral) |
| R = Br | 1.0 | 15 (oral) |
| R = NH₂ | — | 25 (i.p.) |
|  |  | 20 (oral) |
| R = NHCOCH₃ | — | 50 (i.p.) |
| R = NHSO₂CH₃ | 1.0 | 50 (oral) |
| R = CH₃ | 0.1 | 3 (i.p.) |
| R = H  R' = H (dihydrobenzofuran with isobutyl, R' and R substituents) | 0.05 | 20 (i.p.) |
| R = Br  R' = H | 0.005 | 2 (i.p.) |
| R = OCH₃  R' = H | 0.1 | 25 (i.p.) |
|  |  | 1 (oral) |
| R = Cl  R' = Cl | — | 10 (oral) |
| R = H  R' = OCH₃ | — | 25 (oral) |
| R = NH₂  R' = Cl | — | 25 (i.p.) |
|  |  | 50 (oral) |
| R = H  R' = Cl | — | 25 (i.p.) |
|  |  | 40 (oral) |
| R = (piperazinyl-propyl) (benzofuran with Br, amide N-R) | 1.0 | 25 (i.p.) |
|  |  | 5 (oral) |

TABLE VIII-continued
Effects of Benzofuran/Dihydrobenzofuran Compounds
In Vivo Screening Tests
| Structure | Apomorphine Emesis (Dog) 100% Effect Dosage level mg/kg, s.c. | Apomorphine Climbing (Mouse) Approx. 50% ED (mg/kg, s.c.) |
|---|---|---|
| R = 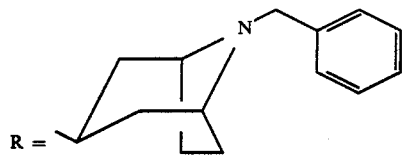 | — | 10 (i.p) 10 (oral) |
| R = 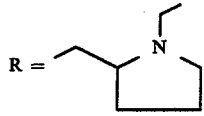 | 0.1 | 0.5 (i.p.) |
| R = 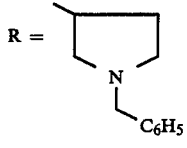 | — | 30 (i.p.) |
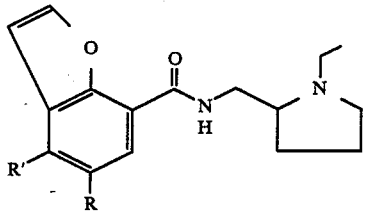
| | | |
|---|---|---|
| R = H R' = H | 10.0 | 12 (i.p.) |
| R = Cl R' = H | 0.1 | 5 (oral) |
| R = Br R' = H | 0.1 | — |
| R = F R' = H | 1.0 | — |
| R = H R' = Cl | — | — |
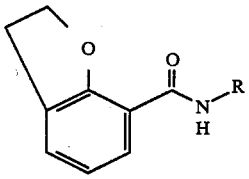
| | | |
|---|---|---|
| R = 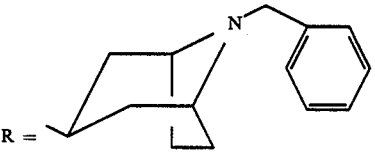 | 1.0 | 20 (i.p.) |
| R = 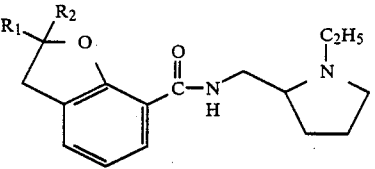 | 1.0 | 20 (i.p.) 15 (oral) |

TABLE VIII-continued

Effects of Benzofuran/Dihydrobenzofuran Compounds
In Vivo Screening Tests

| Structure | Apomorphine Emesis (Dog) 100% Effect Dosage level mg/kg, s.c. | Apomorphine Climbing (Mouse) Approx. 50% ED (mg/kg, s.c.) |
|---|---|---|
| $R_1 = R_2 = H$ | 1.0 | 20 (i.p.) |
| $R_1 = H, R_2 = CH_3$ | 0.85 | 20 (i.p.) |
| $R_1 = R_2 = CH_3$ | 10.0 | 100 (i.p.) |

While the present invention has been described in detail and by reference to specific embodiments thereof, it will be recognized that numerous modifications and variations are possible without departing from the scope of the invention as defined by the following claims.

What is claimed is:

1. A compound of the formula (I):

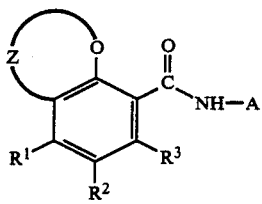

wherein Z represents the carbon atoms necessary to complete a 5- to 7-membered ring, $R^1$, $R^2$, and $R^3$ may be the same or different and one of $R^1$, $R^2$ and $R^3$ is a hydrogen atom and the others are selected from the group consisting of a hydrogen atom, a lower alkyl group, a cycloalkyl group, a halogen atom, an amino group, a lower alkylamino group or dialkylamino group, an alkoxy group, an acylamido group, a sulfonamido group, and a nitro group;

A represents an aminoalkyl moiety selected from the group consisting of:

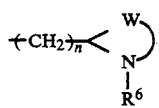 (IV)

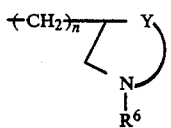 (V)

wherein W represents the carbon and hydrogen atoms necessary to complete a 5 membered ring, Y represents the carbon and hydrogen atoms necessary to complete a 5 membered ring, $R^6$ is selected from the group consisting of a hydrogen atom, a lower alkyl group, a phenyl group, a phenalkyl group, a fluorine substituted lower alkyl group, an allyl group, and a propargyl and n is 0 or an integer of 1 to 3; and acid addition salts thereof.

2. A compound of claim 1 wherein Z represents the atoms necessary to complete a benzo[b]furan or a dihydrobenzo[b]furan ring.

3. A compound of claim 2 wherein A is represented by the formula (IV).

4. A compound of claim 1 wherein said compound is represented by the formula (II):

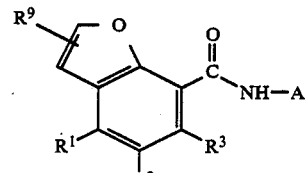

wherein $R^1$, $R^2$, $R^3$, and A are defined as in claim 1; and $R^9$ represents a hydrogen atom, an alkyl group containing 1 to 3 carbon atoms, or a phenyl group, and acid addition salts thereof.

5. A compound of claim 4 wherein A is represented by the formula (IVa).

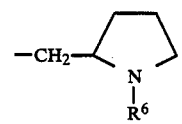 (IVa)

where $R^6$ is defined as in claim 4.

6. A compound of claim 5 wherein $R^9$ is at the 2-position and is a hydrogen atom or a methyl group.

7. A compound of claim 6 wherein A represents a 2-pyrrolidinylmethyl group.

8. A compound of claim 6 wherein A represents a 2-(N-ethyl)pyrrolidinylmethyl group.

9. A compound of claim 1 wherein said compound is represented by the formula (III):

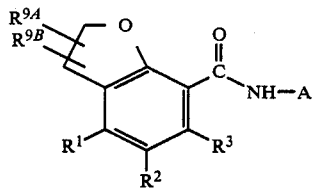

wherein $R^1$, $R^2$, $R^3$, and A are defined as in claim 1; and $R^{9A}$ and $R^{9B}$ can be the same or different and represent a hydrogen atom, an alkyl group having 1 to 3 carbon atoms, or a phenyl group, and acid addition salts thereof.

10. A compound of claim 9 wherein A is represented by the formula (IVa).

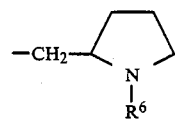 (IVa)

where $R^6$ is defined as in claim 9.

11. A compound of claim 10 wherein $R^{9A}$ and $R^{9B}$ are at the 2-position and represent a hydrogen atom or a methyl group.

12. A compound of claim 1 wherein said compound is represented by the formula (IX):

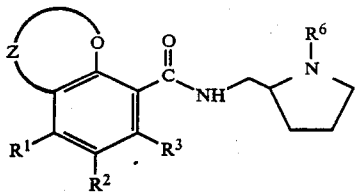

wherein Z represents the atoms necessary to complete a benzo[b]furan ring or a dihydrobenzo[b]furan ring; and $R^1$, $R^2$, and $R^3$ are defined as in claim 1, and $R^6$ represents a hydrogen atom, a lower alkyl group, a phenyl group, a phenalkyl group, a fluorine substituted lower alkyl group, an allyl group, or a propargyl group; and acid addition salts thereof.

13. A compound of claim 12 wherein at least one of $R^1$ and $R^2$ is a halogen atom and $R^3$ is hydrogen.

14. A compound of claim 12 wherein $R^3$ is a methoxy group and $R^1$ and $R^2$ are hydrogen.

15. A compound of claim 12 wherein one of $R^1$ and $R^2$ is an acetoamido group and the other is hydrogen.

16. A compound of claim 12 wherein at least one of $R^1$, $R^2$ and $R^3$ is an amino group or an alkylamino group.

17. A pharmaceutical preparation useful as an antipsychotic or antiemetric agent comprising a pharmaceutically acceptable carrier in combination with a therapeutically-effective amount of a compound of the formula (I) or an acid addition salt thereof:

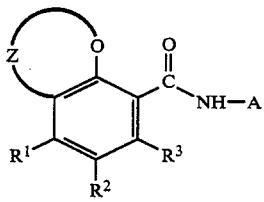

wherein Z represents the carbon atoms necessary to complete a 5- to 7-membered ring;
$R^1$, $R^2$ and $R^3$ may be the same or different and one of $R^1$, $R^2$ and $R^3$ is a hydrogen atom and the others are selected from the group consisting of a hydrogen atom, a lower alkyl group, a cycloalkyl group, a halogen atom, an amino group, a lower alkylamino group or dialkylamino group, an alkoxy group, an acylamido group, a sulfonamido group, and a nitro group; and
A represents an aminoalkyl moiety selected from the group consisting of:

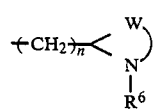 (IV)

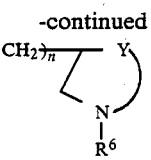 (V)

wherein W represents the carbon and hydrogen atoms necessary to complete a 5 membered ring, Y represents the carbon and hydrogen atoms necessary to complete a 5 membered ring, $R^6$ is selected from the group consisting of a hydrogen atom, a lower alkyl group, a phenyl group, a phenalkyl group, a fluorine substituted lower alkyl group, an allyl group, and a propargyl group; and n is 0 or an integer of 1 to 3.

18. The pharmaceutical preparation of claim 17 wherein A represents a 2-pyrrolidinylmethyl group.

19. A compound of the formula (I):

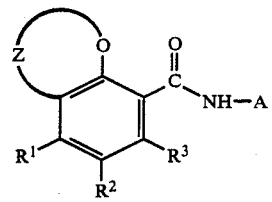

wherein Z represents the atoms necessary to complete a benzo[b]furan ring or a dihydrobenzo[b]furan ring;
$R^1$, $R^2$, and $R^3$ may be the same or different and one of $R^1$, $R^2$ and $R^3$ is a hydrogen atom and the others are selected from the group consisting of a hydrogen atom, an alkyl group having 1 to 6 carbon atoms, a halogen atom, an amino group, an alkylamino group or dialkylamino group in which the alkyl substituent(s) have 1 to 6 carbon atoms, an alkoxy group having 1 to 6 carbon atoms, an acylamido group having 1 to 6 carbon atoms, and a nitro group; and
A represents an aminoalkyl moiety selected from the group consisting of:

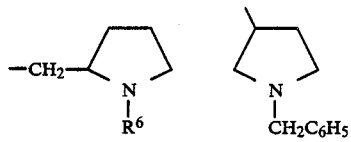

wherein $R^6$ is selected from the group consisting of a hydrogen atom and an alkyl group having 1 to 6 carbon atoms.

20. A compound of claim 19 wherein Z represents the atoms necessary to complete a benzo[b]furan ring.

21. A compound of claim 19 wherein Z represents the atoms necessary to complete a 2,3-dihydrobenzo[b]furan ring.

22. A compound of claim 20 wherein Z represents the atoms necessary to complete a 2-methyl or 3-methyl benzo[b]furan ring.

23. A compound of claim 21 wherein Z represents the atoms necessary to complete a 2-methyl or 3-methyl 2,3-dihydrobenzo[b]furan ring.

24. A compound of claim 19 wherein said compound is represented by the formula (II):

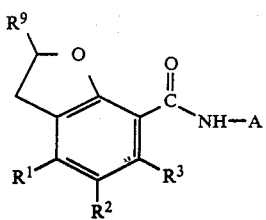

wherein $R^1$, $R^2$, and $R^3$ may be the same or different and one of $R^1$, $R^2$ and $R^3$ is a hydrogen atom and the others are selected from the group consisting of a hydrogen atom, an alkyl group having 1 to 6 carbon atoms, a halogen atom, an amino group, an alkylamino group or dialkylamino group in which the alkyl substitutent(s) have 1 to 6 carbon atoms, an alkoxy group having 1 to 6 carbon atoms, an acylamido group having 1 to 6 carbon atoms, a sulfonamido group having up to 6 carbon atoms, and a nitro group;

A represents an aminoalkyl moiety selected from the group consisting of:

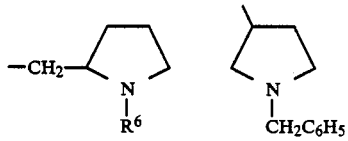

wherein $R^6$ is represent a hydrogen atom or an alkyl group having 1 to 6 carbon atoms and $R^9$ represents a hydrogen atom or an alkyl group having 1 to 3 carbon atoms; and acid addition salts thereof.

25. A compound of claim 24 wherein $R^9$ is hydrogen atom or a methyl group.

26. A compound of claim 25 wherein A represents a 2-pyrrolidinylmethyl group.

27. A compound of claim 19 wherein said compound is represented by the formula (IIIa):

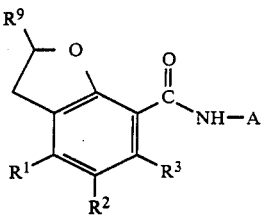

wherein $R^1$, $R^2$, and $R^3$ may be the same or different and one of $R^1$, $R^2$ and $R^3$ is a hydrogen atom and the others are selected from the group consisting of a hydrogen atom, an alkyl group having 1 to 6 carbon atoms, a halogen atom, an amino group, an alkylamino group or dialkylamino group in which the alkyl substituent(s) have 1 to 6 carbon atoms, an alkoxy group having 1 to 6 carbon atoms, an acylamido group having a 1 to 6 carbon atoms, a sulfonamido group having up to 6 carbon atoms, and a nitro group;

A represents an aminoalkyl moiety selected from the group consisting of

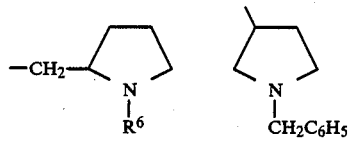

wherein $R^6$ is represent a hydrogen atom or an alkyl group having 1 to 3 carbon atoms; and acid addition salts thereof.

28. A compound of claim 27 wherein $R^9$ represents a hydrogen atom or a methyl group.

29. A compound of claim 28 wherein A represents a 2-pyrrolidinylmethyl group.

30. The compound of claim 1 wherein at least two of $R^1$, $R^2$ and $R^3$ are a hydrogen atom.

31. The pharmaceutical preparation of claim 17 wherein at least two of $R^1$, $R^2$ and $R^3$ are a hydrogen atom.

32. The compound of claim 1 wherein two of $R^1$, $R^2$ and $R^3$ are hydrogen atoms and the other is a methoxy group.

33. The compound of claim 1 wherein two of $R^1$, $R^2$ and $R^3$ are hydrogen atoms and the other is an acylamido group.

34. The compound of claim 1 wherein two of $R^1$, $R^2$ and $R^3$ are hydrogen atoms and the other is a sulfonamido group.

35. The compound of claim 1 wherein two of $R^1$, $R^2$ and $R^3$ are hydrogen atoms and the other is a nitro group.

36. The compound of claim 5 wherein $R^6$ is a hydrogen atom.

37. The compound of claim 10 wherein $R^6$ is a hydrogen atom.

* * * * *

UNITED STATES PATENT AND TRADEMARK OFFICE
CERTIFICATE OF CORRECTION

PATENT NO. : 4,888,353

DATED : December 19, 1989

INVENTOR(S) : Lednicer et al.

It is certified that error appears in the above-identified patent and that said Letters Patent is hereby corrected as shown below:

ON THE TITLE PAGE:

In the ABSTRACT, please delete formula (I) and replace with the following formula (I):

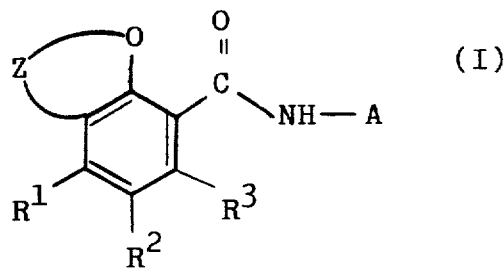

In column 2, line 55, please delete formula (X) and replace with the following formula (X):

UNITED STATES PATENT AND TRADEMARK OFFICE
CERTIFICATE OF CORRECTION

PATENT NO. : 4,888,353
DATED : December 19, 1989
INVENTOR(S) : Lednicer et al

It is certified that error appears in the above-identified patent and that said Letters Patent is hereby corrected as shown below:

Column 21, lines 45-55, please correct the formula by adding a hydrogen atom to the oxygen atom on the phenyl ring.

Column 38, line 55, "(2.5 g, 98.8%)" should be --(2.25 g, 98.8%)--.

Signed and Sealed this

Nineteenth Day of May, 1992

*Attest:*

DOUGLAS B. COMER

*Attesting Officer*     Acting Commissioner of Patents and Trademarks